(12) United States Patent
Zhilov et al.

(10) Patent No.: US 8,592,421 B2
(45) Date of Patent: *Nov. 26, 2013

(54) CYCLIC BIOISOSTERS OF PURINE SYSTEM DERIVATIVES AND A PHARMACEUTICAL COMPOSITION BASED THEREON

(75) Inventors: Valery Khazhmuratovich Zhilov, Moscow (RU); Sergei Vladimirovich Zhuravlev, Moscow (RU); Alexander Nikolaevich Markov, Moscow (RU); Vladimir Mikhailovich Polosin, Moscow (RU)

(73) Assignee: Valery Khazhmuratovich Zhilov, Moscow (RU)

( * ) Notice: Subject to any disclaimer, the term of this patent is extended or adjusted under 35 U.S.C. 154(b) by 1291 days.

This patent is subject to a terminal disclaimer.

(21) Appl. No.: 10/567,114

(22) PCT Filed: Aug. 4, 2003

(86) PCT No.: PCT/RU03/00346
§ 371 (c)(1),
(2), (4) Date: Feb. 3, 2006

(87) PCT Pub. No.: WO2005/012309
PCT Pub. Date: Feb. 10, 2005

(65) Prior Publication Data
US 2008/0194501 A1    Aug. 14, 2008

(51) Int. Cl.
*A61K 31/501* (2006.01)
*A61K 31/706* (2006.01)
*A61K 31/5025* (2006.01)

(52) U.S. Cl.
USPC ............................................ 514/248; 514/43

(58) Field of Classification Search
USPC .................................................. 514/43, 248
See application file for complete search history.

(56) References Cited

U.S. PATENT DOCUMENTS

| | | |
|---|---|---|
| 4,547,507 A | 10/1985 | Clements-Jewery |
| 4,548,817 A * | 10/1985 | Filley et al. ................. 424/717 |
| 4,600,714 A | 7/1986 | Gaitanopoulos et al. |
| 4,612,316 A | 9/1986 | Andersson et al. |
| 4,650,805 A | 3/1987 | Jaen et al. |
| 4,727,079 A | 2/1988 | Bodor |
| 4,904,676 A | 2/1990 | Rae et al. |
| 5,196,432 A | 3/1993 | Crichlow |
| 5,256,660 A | 10/1993 | Swan |
| 5,281,594 A | 1/1994 | Piercey et al. |
| 5,512,573 A * | 4/1996 | Minin et al. .................. 514/248 |
| 5,589,483 A | 12/1996 | West |
| 5,597,820 A | 1/1997 | Hori et al. |
| 5,719,151 A | 2/1998 | Shall et al. |
| 5,723,496 A | 3/1998 | Nakada |
| 5,753,706 A | 5/1998 | Hsu |
| 5,874,444 A | 2/1999 | West |
| 5,883,094 A | 3/1999 | Sanner et al. |
| 5,889,010 A | 3/1999 | Sanner et al. |
| 6,489,326 B1 * | 12/2002 | Abidov et al. ................. 514/248 |
| 6,521,623 B1 | 2/2003 | Monferini et al. |
| 6,953,799 B1 * | 10/2005 | Henry et al. .................. 514/248 |

FOREIGN PATENT DOCUMENTS

| | | |
|---|---|---|
| EP | 0 612 733 A | 8/1994 |
| EP | 0 617 024 A | 9/1994 |
| EP | 1 203 587 A | 5/2002 |
| JP | 50 046697 A | 4/1975 |
| JP | 05-078356 | 3/1993 |
| RU | 2014077 C1 | 6/1994 |

(Continued)

OTHER PUBLICATIONS

Long, JW. The Essential Guide to Prescription Drugs, 1982, Harper & Row, 3rd ed, p. 3-7.*

(Continued)

*Primary Examiner* — Shaojia Anna Jiang
*Assistant Examiner* — Jonathan S Lau
(74) *Attorney, Agent, or Firm* — Locke Lord LLP

(57) ABSTRACT

The invention relates to cyclic bioisosteres of derivatives of a purine system having a general structural formula

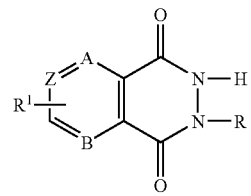

where R=Li, Na, K,

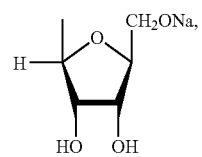

$R^1$=—H, —$NH_2$, —Br, —Cl, —OH, —COOH,
B=—N=, —CH=, Z=—CH=, —N=,
A=—N= at B=—N=, Z=—CH—,
A=—CH= at B=—N=, Z=—CH—,
A=—CH= at B=—N=, Z=—N=,
A=—CH= at B=—CH=, Z=—CH=,
A=—CH= at B=—CH=, Z=—N=,
and their pharmacologically acceptable salts having a normalizing effect on endocellular processes, in particular, it is capable eliminating endocellular metabolic acidosis and capable of binding excessively formed free radicals, in particular, free-radical forms of oxygen, capable of normalizing the nitrergic mechanisms of the cells, and also capable of interreacting with adenosine-sensitive receptors on the membrane of non-nuclear cells and in nuclei-containing cells to decrease the aggregation of thrombocytes. The compounds according to the invention have hepatoprotective effect and can be used for producing pharmaceutical compositions on their base.

4 Claims, 7 Drawing Sheets

(56) References Cited

FOREIGN PATENT DOCUMENTS

| | | |
|---|---|---|
| RU | 2098086 | 10/1997 |
| RU | 2108806 | 4/1998 |
| RU | 2113222 | 6/1998 |
| RU | 2 168 511 | 8/1998 |
| RU | 2132188 | 6/1999 |
| RU | 2132189 | 6/1999 |
| RU | 2132685 | 7/1999 |
| RU | 2138264 | 9/1999 |
| RU | 2155043 | 8/2000 |
| RU | 2160104 | 12/2000 |
| RU | 2 163 122 | 2/2001 |
| RU | 2163122 | 2/2001 |
| RU | 2167659 | 5/2001 |
| RU | 2 169 139 | 6/2001 |
| RU | 2169139 | 6/2001 |
| RU | 2 185 173 | 7/2002 |
| RU | 2 211 036 | 8/2003 |
| WO | WO0172305 | 10/2001 |
| WO | 02/09681 A | 2/2002 |

OTHER PUBLICATIONS

Frank et al. Nat. Rev. Drug Discov., 2003, 2(7), p. 566-580.*

Levraut et al., Current Opinion in Critical Care, Aug. 2003, 9(4), p. 260-265.*

Gonzalez et al., American Journal of Physiology, 1975, 228(4), p. 1060-1064.*

Gores et al., J. Clin. Invest., 1989, 83, p. 386-396.*

U.S. Appl. No. 10/567,113, filed Aug. 3, 2004, Zhilov et al., WO 05/011648, Feb. 10, 2005.

Trump B.F, Berezesky I.K. "The role of altered [$Ca^{2+}$] in regulation in apoptosis, oncosis and necrosis". Biochem. Biophys. Acta, 1996, v. 1313, p. 173-178.

Roos A., Boron W.F. "Intracellular pH". Physiol. Rev., 1981, v. 61, p. 296-434.

Akotov V.S., Grobova M.E., Rkshevoi Yu.V. "Intracellular pH and substrate dependence of proliferation of fibroblasts of Chinese hamster". Cytology, 1991, 33 (7), p. 86-94.

Gillies R.G., Martinez-Zaguilan R., Peterson E.P., Perona R. "The role of intracellular pH in mammalian cell proliferation". Cell. Physiol. Biochem., 1992, 2, p. 159-179.

Akatov V.S., Grobova M.E. "Activation of intracellular pH regulating systems upon cell adhesion to solid substrate". Biol. Membr., 1993, v.6, p. 917-934.

Kapus A., Romanek R., Qu A.Y.Rotstein O.O., Grinstein S.A. "pH-sensitive and voltage-dependent proton conductance in the plasma membrane of macrofages". J. Gen. Physiol., 1993, vol. 02 (4), p. 723-760.

Demaurex N., Downey G., Waddell T., Grinstein S. "Intracellular pH regulator during spreading of human neutrophils", J.Cell. Biol., 1996, v. 133, p. 1381-1402.

Tannock I.A., Rotin D. "Acid pH in tumors and its potential for therapeutic exploration". Cancer Res., 1989, v.49, p. 4373-4384.

Stabbs M., Rodrigues L., Howl F.A., Wang I., Joeng K.S., Veech R.L., Griffiths J.R."Metabolic consequences of a reversed pH gradient in rat tumors". Cancer Res., 1994, v.54, p. 4011-4016.

Mashkovsky M.D., "Medicinal Agents". Moscow, Medicine, 1993, part II, p. 137-140.

Taguchi Hiroshi. "A new fluorometric assay method for guinolinic acid". Analitic Biochemistry, 1983, 131 (1), p. 194-197.

Huntress E.H., Stanley L.N., Parker A.S. "The preparation of 3-Aminophtalhydrazide for use in the Demonstration of Chemiluminescence", J, Am. Chem. Soc., 1994, v. 56, p. 241-242.

Zyczynska-Baloniak I., Czajka R., Zinkowska E., Synthesis of Derivatives of 4-Hydroxypyrazine-[2,3-d]pyridazine-I-one. Polish Journal of Chemistry. 1978, v. 52, p. 2461-2465.

Kormendy K., Ruff F. "Pyridazines condensed with a Heterering. Ш"., Acta Chimika Hungarika. 1990, 127 (2), p. 253-262.

Yurugi S., Hieda M. "Studies on the synthesis of N-Heterocyclic Compounds". Chemistry, Pharmaceutic Bull., 1972, v. 20 (7), p. 1522-1527. ibid., p. 1513-1521.

Seo E., Kuwana T. "Polarography of cyclic Hydrazides", J. Electroanal. Chem., 1963, v. 6, p. 417-418.

Lund H. "Polarographic and electropreparative reduction of 1(2H)-phthalazines, 2,3-dihydro-I,4 phthalazindiones and related compounds", Coll. Czechoslow. Chem.Com., 1965, v. 30. p. 4237-4249.

Ganz M.B. et all. "Argininvasopression enchangers of pH, regulation in the presence of $HCO_3^-$ by stimulating three acid-base transport systems", Nature, 1989, v. 337, p. 648-651.

Rogachev B., Hausmann M.J., Julzari R., Weiler H., Holmes C., Falct D., Chaimovitz C., Douvdevani A. Effect of bicarbonat-based dialysis solution on intracellular pH (pH;) and TNF-alpha production by peritoneal macrophages, Perit. Dial. Int., Nov.-Dec. 1997, 17 (6), p. 543-553.

Bidani A., Heming T.A. "Effect of concanavalin A on $Na^+$-dependent and $Na^+$-independent mechanism for $H^+$ extrusion in alveolar macrophages", Lung., 1998, 176 (1), p. 25-31.

Swallow C.J., Grinstein S., Sudsbury R.A., Rotstein O.D. "Relative roles of $Na^+/H^+$ exchange and vacuolar-type $H^+$ ATPases in regulating cytoplasmic pH and Function in murine peritoneal macrophages", J. Cell. Physiol., 1993, 157 (3), p. 453-460.

Koshevoi Yu.V., Akatov V.S., Grobova M.E., "Microspectrofluorimeter for measuring endocellular pH (micro pH)". Devices and equipment for studies in the field of physical-and-chemical biology and biotechnology. Pushchino, 1990. p. 8-14.

Thomas J.A., Bushbaum R.N., Zimniak A.w Racker E. "Intracellular pH measurements in Ehrlich ascites tumor cells utilizing spectroscopic probe generated in situ", Biochemistry, 1979, v. 18, p. 2210-2218.

Li J., Eastman A. "Apoptosis in an interleukin-2-depended cytotoxic T-lymphocyte cell line is associated with intracellular acidification", J.Biol. Chem., 1995, v. 270. , No. 7, p. 3203-3211.

Solovieva M.E., Akatov V.S., Leshchenko V.V., Kudryavtsev V.A. "The mechanism of destruction of cells of myeloma NS/O in culture". Proceeding of the Russian Academy of Sciences, 1998, 2, p. 194-189.

Zhu W.-H., Loh T.-T. "Effects of Na+/H+ antiport and intracellular pH in the regulation of HL-60 cell apoptosis", Biochim. Biophys. Acta, 1995, v. 1269, p. 122-128.

Brenton P.D. "Mechanistic Aspect of Diazaquinone Chemiluminescence", Aust. J. Chem., 1984, v. 37, p. 1001-1008.

Nishikimi M. Rao N.A. and Yagi K. "The occurrence of superoxide anion in the reaction of reduced phenasine methosulfate and molecular oxygen". Biochem Biophys. Res. Commun, 1972, v. 46, p. 849-855.

Rahman S., Ali Khan R., Kumar A. "Experimental study of the morphine deaddiction properties of Delphinium denudatum Wall// BMC Complement Altern". Med. 2002, v. 29, p. 1-6.

Dum J., Blasig J., Herz A. Buprenorphine: "Demonstration of physical dependence liability". Eur. J. Pharmacol., 1981, v. 70. p. 293-300.

Misko T.R., Schilling R.J., Salvemini D. et al. "A fluorometric assay for the measurement of nitrite of biological samples". Anal. Biochem., 1993, v. 214, p. 11-16.

Bredt and Snyder. "Nitric oxide mediates glutamate-linked enhancement of cGMP levels in the cerebellum". Proc. Natl. Acad. Sci. USA, 1989, v. 86, p. 9030-9033.

Kiss J.P., Vizi E.S., "Nitric oxide: a novel link between synaptic and nonsynaptic transmission," Trends Neurosci., Apr. 2001, 24 (4):211-5.

Paul I.A., Skolnick P., "Glutamate and depression: clinical and preclinical studies," Ann. N Y Acad. Sci., Nov. 2003; 1003:250-72.

Girgin Sagin F., Sozmen E.Y., Ersoz B., Mentes G., "Link between monoamine oxidase and nitric oxide," Neurotoxicology, Jan. 2004, 25 (1-2): 91-9.

Vizi E.S., "Role of high-affinity receptors and membrane transporters in nonsynaptic communication and drug action in the central nervous system," Pharmacol. Rev., Mar. 2000, 52 (1): 63-89.

Liu Y., "Nitric oxide effect dopaminergic processes", Adv. Neuroimmunol., 1996, 6 (3): 259-64.

Chiavegatto S., Nelson R.J., "Interaction of nitric oxide and serotonin in aggressive behavior," Horm. Behav., Sep. 2003, 44 (3): 233-41.

(56) References Cited

OTHER PUBLICATIONS

Pfaus J.G., "Neurobiology of sexual behavior", Curr. Opin. Neurobiol., Dec. 1999, 9 (6): 751-8.

Stefano G.B. "Autoimmunovascular regulation: morphine and anandamide and ancondamide stimulated nitric oxide release", J.Neuroimmunol., Mar. 1998, 15, 83 (1-2): 70-6.

Tayfun Uzbay I., "Oglesby M.W. Nitric oxide and substance dependence," Neurosci. Biobehav. Rev., Jan. 2001, 25 (1): 43-52.

Kiss J.P. "Role of nitric oxide in the regulation of monoaminergic neurotransmission", Brain Res. Bull., Aug. 2000, 52 (6): 459-66.

Mandel S., Grunblatt E., Riederer P., Gerlach M., Levites Y., "Youdim M.B. Neuroprotective strategies in Parkinson's disease: an update on progress", CNS Drugs, 2003, 17 (10): 729-62.

Ujike H., "Advanced findings on the molecular mechanisms for behavioral sensitization to psychostimulants", Nippon Yakurigaku Zasshi., Jan. 2001, 117 (1): 5-12.

Olesen J., Jansen-Olesen I., "Nitric oxide mechanisms in migraine." Pathol. Biol., Paris, Sep. 2000, 48 (7): 648-57.

Missale C., Nash S.R. Robinson S.W., Jaber M., Caron M.G., "Dopamine receptors: from structure to function", Physiol. Rev., Jan. 1998, 78 (1): 189-225.

Zawilska J.B. "Dopamine receptors-structure, characterization and function", Postepy. Hig. Med. Dosw., 2003, 57 (3): 293-322.

Fagen Z.M., Mansvelder H.D., Keath J.R., Mc. Gehee D.S., "Short- and long-term modulation of synaptic inputs to brain reward areas by nicotine", Ann., NY Acad. Sci., Nov. 2003, 1003: 185-95.

Ujike H., "Molecular biology of drug dependence and behavioral sensitization", Seishin Shinkeigaku Zasshi., 2002, 104 (11): 1055-68.

Wolf M.E., Mangiavacchi S., Sun X., "Mechanisms by which dopamine receptors may effect synaptic plasticity", Ann. NY Acad. Sci., Nov. 2003, 1003: 241-9.

Kosten T.R., George T.P., Kosten T.A., "The potential of dopamine agonists in drug addiction", Expert Opin. Investig. Drugs, Apr. 2002, 11 (4): 491-9.

Pearlson G.D. "Neurobiology of schizophrenia", Ann. Neural., Oct. 2000, 48 (4):556-66.

Abi-Dargham A., Moore H. , "Prefrontal DA transmission at D1 receptors and the pathology of schizophrenia", Neuroscientist, Oct. 2003, 9 (5): 404-16).

Conley R.R., Kelly D.L. "Current status of antipsychotic treatment" Curr. Drug Target CNS. Neurol. Disord., Apr. 2002, 1 (2): 123-8.

Taylor D.P., Riblet L.A., Stanton H.C., Eison A.S., Eison M.S., Temple DL Jr.. "Dopamine and antianxiety activity", Pharmacol, Biochem. Behav., 1982, 17, Suppl. 1: 25-35.

Kapur S., Mamo D. "Half a century of antipsychotics and still a central role for dopamine D2 receptors", Prog. Neuropsychopharmacol. Biol. Psychiatry, Oct. 2003, 27 (7): 1081-90.

Taguchi Hiroshi. "A new fluorometric assay method for quinolinic acid". Analitic Biochemistry, 1983, 131 (1), p. 194-197.

Dum J, Blasig J, Herz A, "Buprenorphine: demonstration of physical dependence liability", Eur. J. Pharmacol., 1981, V. 70, p. 293-300.

Rahman S., Ali Khan R., Kumar A., "Experimental study of the morphine de-addiction properties of Delphinium denudatum Wall", BMC Complement Altern. Med., 2002, V.29, p. 1-6.

Blasig J., Herz A., Reinhold K., Zieglgansberger S. "Development of physical dependence on morphine in respect to time and dosage and quantification of the precipitated withdrawal syndrome in rats", Psychopharmacologia, Berlin, 1973, V.33, p. 19-38.

Rahman S., Ali Khan R., Kumar A. "Experimental study of the morphine de-addiction properties of Delphinium denudatum" Wall, BMC Complement Altern. Med., 2002, V.29, p. 1-6.

Misko T.R., Schilling R.J., Salvemini D. et al. "A fluorometric assay for the measurement of nitrite in biological samples", Anal. Biochem., 1993, V. 214, p. 11-16.

Lei B., Adachi N., Nagaro T., Arai T. "Measurement of total nitric oxide metabolite (NO (x) (−)) levels in vivo. Brain", Res. Protoc., 1999, V. 4, p. 415-419.

Bredt M., Snyder S. "Nitric oxide mediates glutamate-linked enhancement of cGMP levels in the cerebellum", Proc. Natl. Acad. Sci., USA, 1989, V.86, p. 9030-9033.

Bradford M. M. "A rapid and sensitive method for quantitation of microgram quantities of protein using the principle of protein binding" Anal. Biochem., 1976, V. 72, p. 248-254.

Giuliano F., Allard J. "Dopamine and male sexual function" Eur. Urol., 2001, 40 (6), 601-608.

iuliano F., Allard J., Rampin O. et. al. "Pro-erectile effect of systemic apomorphine: existence of a spinal site action" J. Urol., 2002, 167 (1), 402-406.

Brien S.E., Smallegange C., Gofton W.T., et.al. "Development of a rat model of sexual performance anxiety: effect of behavioral and pharmacological hyperadrenergic stimulation on apomorphine-induced erections" Int. J. Impot. Res., 2002, 14 (2), 107-115.

\* cited by examiner

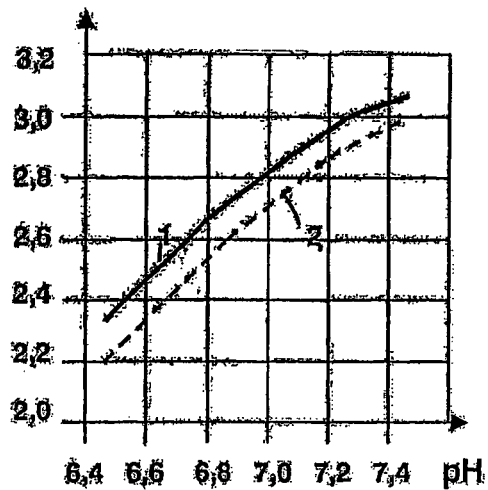
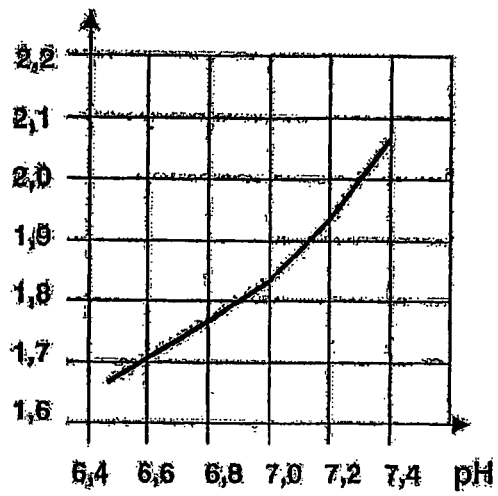
FIG. 1a                    FIG. 1b
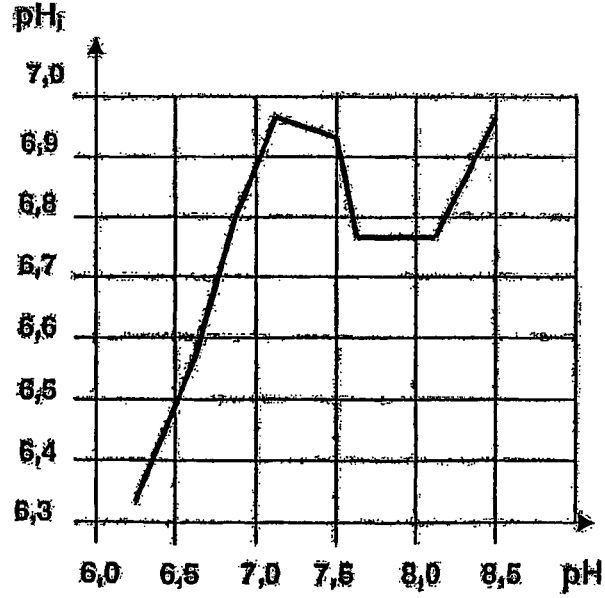
FIG. 2

CYCLIC BIOISOSTERS OF PURINE SYSTEM DERIVATIVES AND A PHARMACEUTICAL COMPOSITION BASED THEREON

This is a US national phase application under 35 U.S.C. §371 of international application PCT/RU2004/000298, filed Aug. 3, 2004, hereby incorporated by reference in its entirety, which is a continuing application of, and claims benefit under 35 U.S.C. §120 to, co-pending international application PCT/RU2003/000246, filed Aug. 4, 2003, which designated the United States of America and of which is hereby incorporated by reference in its entirety.

FIELD OF THE INVENTION

The invention relates to medicine, in particular, to pharmaceutical compositions for treatment of various diseases and, more specifically, the invention relates to the medicinal agents that have an appreciable normalizing effect on endocellular processes, in particular, elimination of an endocellular metabolic acidosis and binding of excessively formed free radicals.

PRIOR ART

It is well known that the homeostatic parameters providing survival of an organisms and inseparably linked with each other are mainly a content of gases $O_2$ and $CO_2$ in blood, a content of electrolytes $Na^+$, $K^+$, $CL^+$, $HCO_3^-$ and acid-base balance of a cell. The content of gases in blood characterizes oxidation-reduction processes in a cell, oxygen being an important participant of the process of oxidation and carbon dioxide being a product of oxidation reactions. Electrolytes make a basis of an exocellular and endocellular medium, a basis for cellular integration for functioning of nervous and muscular tissue.

The content of hydrogen ions $H^+$ is an objective characteristic of the acid-base balance: the hydrogen ions provide a bond between the electrolytes and the blood gases through a buffer system ($HCO_3^-$—$CO_2$). Besides, the activity of the enzymatic systems depends on the content of hydrogen ions $H^+$: enzymes are usually most active in a narrow range of concentration of hydrogen ions. For each enzyme there is a definite range of pH values, in which the enzyme shows the maximum activity, for example, for α-ptyalin and for catalase pH 6.8 to 7.0, for urease pH 7.0 to 7.2, for trypsin pH 7.5 to 8.5; beyond these ranges the activity of enzymes drops down drastically.

The effect of a change in pH of a medium on the behavior of an enzyme molecule depends, in particular, on the degree of ionization of the COOH— groups of dicarboxylic aminoacids, SH-groups of cysteine, imidazole nitrogen of histidine, $NH_2$-group of lysine and other groups. At a significant difference of the pH of a medium from the optimal values the enzymes are exposed to conformational changes resulting in a loss of activity owing to a denaturation or a change of the enzyme molecule charge. At different pH values of the medium the active center of the enzyme can be in a partially ionized state or in non-ionized state that adversely affects the tertiary protein structure and, respectively, on the formation of an active enzyme-substrate complex.

Besides, pH of a medium has an effect on the rate of ionization of substrata and coenzymes.

For a cell it is important to maintain the acid-base balance, i.e. formation of hydrogen atoms $H^+$ and their removal from the cell. The absolute or relative increase of a hydrogen ion concentration in a medium makes it acidic and a decrease-alkaline. The concentration of $H^+$ in blood plasma under normal condition of an organism makes about $10^{-7}$. The value of pH in blood is very stable and normally varies from pH 7.35 to 7.45. A deviation of pH results in abnormal functioning of the cells and, first of all, of their numerous enzymatic systems, a change of direction and intensity of the oxidation-reduction processes, for example, the ability of haemoglobin to bind and give back oxygen. In this case all metabolic processes and, first of all, aqueous and electrolytic metabolism change, the sensitivity of the cellular receptors is disturbed, the permeability of membranes, nervous-muscle excitability and conduction are changed.

The physiological systems participate in the maintenance of pH values for normal vital activity of the blood and tissues: lungs, liver, kidneys, gastric path and buffer systems: haemoglobin, bicarbonate, protein and phosphatic. The buffer systems rather quickly and effectively prevent a shift of the acid-base balance but they are not capable to keep it for a long time without participation of the physiological systems.

When the capability of the above compensatory systems by the maintenance of the hydrogen concentration is exhausted, the acid-base balance is disturbed, in which case two different states can arise: acidosis, when the concentration of hydrogen ions is higher than the optimum concentration (pH is below the optimum value) and alkalosis. A decrease of pH below 6.8 is incompatible to life.

The metabolic acidosis is the most serious and most frequently encountered form of disorder of the acid-base balance. The metabolic acidosis can be a result of hypoxia of any origin: exogenous, circulatory, respiratory, tissue, hemic, as well as sugar diabetes, starvation, fever, renal failure, long diarrhea, extensive inflammations, for example, peritonitis, overdosage of calcium chloride, and other diseases. The kidneys and liver try to compensate for the acidosis: acido- and ammoniogenesis is activated in the renal canals, if the metabolic acidosis is not a consequence of renal failure, and the reabsorption of bicarbonate in the kidneys is intensified to withdraw it from the liver.

As a rule, the concentration of ions $K^+$ in plasma increases due to their replacement from the cells by ions $H^+$. The protein binds ions $H^+$ and release ions $K^+$ and $Na^+$ in the plasma. The increase of the osmotic pressure of the plasma due to hypematremia promotes discharge of water from the cells and development of a hyperosmolar syndrome.

Metabolic acidosis leads to pathological changes: the vessels, as a rule, expand at a moderate decrease of pH and narrow at an evident acidosis; at a decrease of the vascular tone the arterial and venous pressure drop down, the venous return to the heart decreases so that the stroke and minute heart volume decreases. The sensitivity of the myocardiocitus to calcium ions and to adrenaline decreases and this is accompanied by a decrease retractive ability of the myocardium.

Hyperpotassemia with a content in ions $K^+$ in the plasma exceeding 5.2 mmol/l entails disorder of the nerve-and-muscle conduction and originates such symptoms as an increased tonus of the transversospinal muscle, vomiting, diarrhea, mental disorder, sensitivity disorder, bradycardia, extrasystole. When the concentration of ions $K^+$ in the plasma is higher than 7.5 mmol/l, a development of a ventricular fibrillation of heart and stopping it in the diastole, as well as paralysis of the skeletal musculation are possible. The aggregation and agglutination of thrombocytes rise up and the emerging microthrombuses break the microcirculation, aggravating the hypoxia, causing disorder of the metabolic processes and strengthen the acidosis.

The disorder of the heart activity and peripheral blood circulation result in repeated malfunction of the kidneys, liver, and the central nervous system. In serious cases the coma develops that can lead to stopping the respiration.

At an excessive decrease of pH in the cell (less than 6.8) the cell lysosomes are destroyed and the cells are subjected to autolysis under the effect of lysosomal enzymes.

The development of authentic methods of intravital pH-metering of cells has allowed us to determine that the changes in the endocellular pH accompany many major processes on the cellular level. Some factors point to the fact that for normal vital activity of the cells and tissues of an organism the maintenance of pH in a definite range is necessary. A plausible reason may be high sensitivity of the basic cellular enzymes to the pH value. For example, it is known that the activity of one of the key enzymes of glycolysis 6-phosphofructokinase [2.7.1.11] grows by dozens of times at an increase of pH in a medium by 0.2 units (Trump B. F, Berezesky I. K. "The role of altered [$Ca^{2+}$] in regulation in apoptosis, oncosis and necrosis". Biochem. Biophys. Acta, 1996, v. 1313, p. 173-178).

The activity of Pyruvatcarboxylase [6.4.1.1], phosphorylases [2.4.1.1] catalyzing the glycogen metabolism also depends on the pH value, and their activity is inhibited at a rising pH of cytoplasm (Roos A., Boron W. F. "Intracellular pH". Physiol. Rev., 1981, v. 61, p. 296-434).

It is well known that there is a correlation between processes of attachment of substrate cells, an increase of pH and a start of the mechanism of proliferation of the minimally transformed cells (Akopov V. S., Grobova M. E., Rkshevoi Yu. V. "Endocellular pH and substrate dependence of proliferation of fibroblasts of Chinese hamster". Cytology, 1991, 33 (7), p. 86-94; Gillies R. G., Martinez-Zaguilan R., Peterson E. P., Perona R. "The role of intracellular pH in mammalian cell proliferation". Cell. Physiol. Biochem., 1992, 2, p. 159-179; Akatov V. S., Grobova M. E. "Activation of intracellular pH regulating systems upon cell adhesion to solid substrate". Biol. Membr., 1993, v. 6, p. 917-934).

It has been found that a decrease of pHi in macrophages inhibits the production of superoxide and phagocytic activity. Besides, the activation of phagocytes results in a protons yield that, in turn, results in rising the pH value (Kapus A., Romanek R., Qu A. Y. Rotstein O. O., Grinstein S. A. "pH-sensitive and voltage-dependent proton conductance in the plasma membrane of macrofages". J. Gen. Physiol., 1993, vol. 02 (4), p. 723-760).

A change of pHi is considered as a possible mediator of spreading and chemotaxis of neutrophils, and a strict correlation of pHi is necessary for successful fulfillment of the microbiocide function (Demaurex N., Downey G., Waddell T., Grinstein S. "Intracellular pH regulator during spreading of human neutrophils", J. Cell. Biol., 1996, v. 133, p. 1381-1402).

On the basis of the above data one may make a true conclusion that an increase of endocellular pHi is an indication of activity of cells. Therefore, using the knowledge on the pH value and on ways and methods of maintenance of this parameter in a definite range, it is possible to act on the endocellular processes efficiently.

For example, in the prior art there are known researches on development of medicinal preparations capable of selectively collecting in the cells of tumors, differing from the normal cells by the pHi value (Tannock I. A., Rotin D. "Acid pH in tumors and its potential for therapeutic exploration". Cancer Res., 1989, v. 49, p. 4373-4384; Stabbs M., Rodrigues L., Howl F. A., Wang I., Joeng K. S., Veech R. L., Griffiths J. R. "Metabolic consequences of a reversed pH gradient in rat tumors". Cancer Res., 1994, v. 54, p. 4011-4016)

A possibility of a predicted change of the endocellular pHi has practical importance for regulation of the endocellular metabolism. Therefore, development of pharmaceutical compositions capable of effectively increasing pHi is an urgent task.

Known in the art is application of ferruginous compounds, including iron citrate and acetate and their combinations in the case of hyperphosphatemia, as a means for decreasing the phosphorus content and for correcting the metabolic acidosis at renal failure (U.S. Pat. No. 5,753,706) on the basis of absorption of absorbed phosphases in an intestine.

Also known in the art a veterinary composition for treatment or prevention of a lactate acidosis containing alpha-2-adrenoceptor antagonist from the group of imidazolines, benzodioxfnoimidazolines and benzofuquinolines (U.S. Pat. No. 5,196,432).

Known in the art is a method of protection of human cells against irreversible disorders brought on by a lactate acidosis due to oxygen failure, preferably, cells of the central nervous system, said method comprising introduction into an organism of a non-toxic compound capable of penetrating through the cell membrane or to overcome the hematoencephalic barrier, which can perform a protective buffer function in the cell and tissues, interfering with an increase of the concentration of hydrogen ions while supporting the pH within physiologically acceptable limits (not lower than 6, 8), taken from the group including $N_2C_2CH_2SO_3H$, $NH_2-C(NH)NH(CH_2)_2SO_3H$ or $NH_2-C(NH)NH(CH_2)_2SO_3Na$ (U.S. Pat. No. 5,312,839, A).

Application of derivatives of 1,4-benzoxazine is known as a medicinal agent for treatment of diseases caused by an endocellular acidosis at miocardial ischemia (U.S. Pat. No. 5,597,820, A).

Known in the art is a drug of hemodynamic action as an aqueous solution of dextran with a molecular weight of 40000 with addition of salts: sodium chloride, potassium chloride, magnesium chloride, calcium chloride and sodium acetate for normalization of the acid-base balance and electrolytic balance (RU, 2185173, C2) A high concentration of a complex of salts compared to preparations dextran 40 (USA) and dextran 70 (USA) effectively compensates the deficiency of salts of blood and intertissue liquid, and corrects metabolic acidosis more effectively. Presumably, sodium acetate introduced into an organism takes part in the metabolism and the $CH_3COO-$ anion turns into water and carbon dioxide, and the cation $Na^+$ reacts with underoxidized acid products of the metabolism and recovers the pH of the medium. However, the recovery of the pH of the medium not always results in irreversible recovery of the pHi of the cell.

Application of namacite (carbostimuline) containing bicarbonate, salts of magnesium, manganese and zinc and sodium citrate is known and used for integrated correction of metabolic acidosis, the activity of the drug being a result of interaction of carbon dioxide with the enzymatic protein resulting in a change of the enzyme activity with respect to the complex of reactions of a carboxylation and decarboxylation in the tissues; the ions of magnesium, manganese and zinc activate carboxylases, and sodium citrate serves as a substrate for reactions of a cycle of tricarboxylic acids, lipogenesis (RU, 2014077, C1).

Known in the art is a method of treatment of Alzheimer's disease due to disorder it is beta-amyloid-peptide metabolism which is growing out of the endocellular acidosis, mainly lactate acidosis, or fluctuation of pH from the normal pH value 7.3 and acid endocellular pH between 5.0 and 7.0 comprising administration to the patient of a pharmacologically effective quantity of an alkaline compound or a buffer capable of rising the endocellular pH from 7.0 to a range of 7.1 to 7.4 and to overcome the hematoencephalic barriers to pass through the cellular membrane to reduce the concentration of hydrogen ions and to have pH from 6.8 to 11.4, namely, the compounds from the group of guanidinethane sulfate, guanidinethane of sulfonic acid and other compounds (U.S. Pat. No. 5,723,496).

Sodium bicarbonate is used to cure various diseases accompanied by evident acidosis, to beat acidosis during surgical interventions. It is also used as antacid agent at hyperoxemia of gastric juices, at a peptic ulcer of a stomach and duodenal intestine. However, during its application it should be kept in mind that its long administration to an organism can result in uncompensated alkalosis accompanied by serious disorders of the acid-base blood condition.

Known in the art is preparation trisamine, which includes an active material comprising tri-(oxymethyl)aminomethane, being an antiacid of systemic action (U.S. Pat. No. 5,256,660, A). The trisamine is used at the acute and chronic diseases accompanied by metabolic and mixed acidosis. The preparation is applied intravenously as a 3.66% solution. Trisamine binds a plenty of ions $H^+$ and deduces them with urine, therefore, it is applied only at normal functioning of kidneys. On the other hand, trisamine promotes an increase of the content of ions $HCO_3^-$ in blood. However, trisamine is contraindicative at disorder of excretory function of kidneys and functional disorders of a liver. Since the preparation also initiates respiratory depression, the patients with failure of ventilation of the lungs are treated with it only under conditions of controlled or assisted breathing.

At present, in the medical practice metabolic acidosis is eliminated in several steps. At the initial step solutions of sodium bicarbonate or trisamine is used.

At the following step measures are taken for normalization of the hemodynamics and the gas exchange, improvement of the blood microcirculation and metabolic processes in the organism, correction of the electrolytic misbalance to ensure elimination of the reason caused the shift of the acid-base balance.

Also known in the art is a medicinal preparation <<dimephosphon>>, containing dimethyl ester of 1,1-dimethyl-3-oxybuthyl of phosphonic acid as an active material (Mashkovsky M. D., "Medicinal Agents". Moscow, Medicine, 1993, part II, p. 137-140) whose antiacidotic effect is associated with the activation of metabolic processes, regulation of the acid-base balance of an organism including pneumonia and acute respiratory diseases. However, the application of this drug can cause dyspeptic disorder.

The development of medicinal preparations eliminating endocellular metabolic acidosis and rendering normalizing effect on the endocellular processes is and actual problem.

DISCLOSURE OF THE INVENTION

An object of the present invention is to produce a medicinal agent for correction of disorders of endocellular processes.

Another object of the invention is to provide a medicinal agent based on compounds having biological activity for normalization of the acid-base balance of a cell due to withdrawal from the cell of excessive quantity of protons thereby increasing the cell pH, normalizing the activity of the enzymatic systems, normalizing the direction and intensity of the oxidation-reduction processes through interaction with adenosine-sensitive receptors on the membrane and inside the cell and binding of excessively formed free radicals.

The biologically active compounds having properties necessary for attaining the above objects are based on derivatives of condensed pyridazinedione systems, which, in the inventors' opinion can have cyclic isosterism with respect to adenosine, because they contain ring systems similar to adenosine by size and character of the electron density.

The inventors assumed that the condensed pyridazinedione systems having a structure similar to adenosine may have similar reactivity in an organism, are capable of attracting β-D-ribofuranous fragments, and react with receptors sensitive to adenosine and penetrate through the cellular membrane i.e. can be the biological isosteres of adenosine. At the same time, they are electrochemically active compounds with sufficiently low potentials of reduction and can attach 2-4 protons and electrons thus eliminating the endocellular metabolic acidosis.

The object of the invention was attained by providing cyclic bioisosteres of a purine system having a general formula:

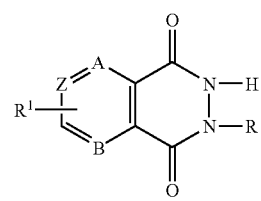

Where R=Li, Na, K,

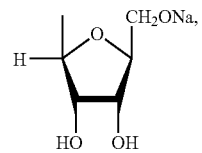

$R^1$=—H, —$NH_2$, —Br, —Cl, —COOH,
B=—N=, —CH=, Z=—CH=, —N=,
A=—N= at B=—N=, Z=—CH—,
A=—CH= at B=—N=, Z=—CH—,
A=—CH= at B=—N=, Z=—N=,
A=—CH= at B=—CH=, Z=—CH=,
A=—CH= at B=—CH=, Z=—N=, and their pharmacologically acceptable salts having a normalizing effect on endocellular processes.

The derivatives of pyrido[2,3-(d]-6H-pyridazine-5,8-dione, cyclic bioisostere of derivatives of purine system were synthesized and investigated, in which the pyridine ring is condensed with a pyridazinedione ring having a general formula:

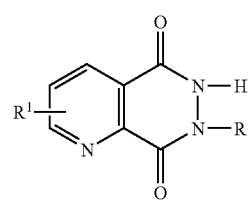

Where R is the atom of Li, Na, K,

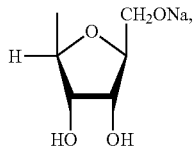

R₁ is —H, —NH₂, —Br, —OH, —COOH,
in particular:
sodium salt of 7-(β-O-ribofuranosile)pyrido[2, 3-1]-6H-pyridazine-5,8-dione sodium salt (1),
4-amino-7-(β-D-ribofuranosile)pyrido[2,3-d]-6H-pyridazine-5,8-dione (2),
sodium salt of 3-bromine-7-β-B-ribofuranosile)pyrido[2,3-d]-6H-pyridazine-5,8-dione (3),
disodium salt of 4-hydroxy-7-(βD-ribofuranosile)pyrido[2,3-d]-6H-pyridazine-5,8-dione (4),
disodium salt of 3-карбоксћ-7-(β-D-ribofuranosile)pyrido[2,3-d]-6H-pyridazine-5,8-dione (5),
lithium salt of pyrido[2,3-d]-6H-pyridazine-5,8-dione (6),
sodium salt of pyrido[2,3-d]-6H-pyridazine-5,8-dione (7),
potassium salt of pyrido[2,3-d]-6H-pyridazine-5,8-dione (8).

There were also synthesized and investigated derivatives of benzo[d]-3H-pyridazine-1,4-dione, cyclic bioisostere of a derivative purine system, in which the benzene ring condensed with pyridazinedione ring having a general formula:

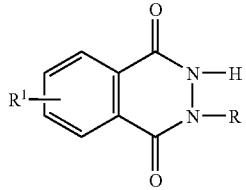

where R=

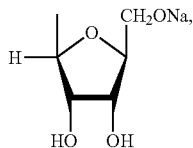

Li, Na, K,
R¹=—H, —NH₂, —Cl, —OH, —COOH,
in particular:
sodium salt of 2-(β-D-ribofuranosile)benzo[d]-3H-pyridazine-1,4-dione (9),
sodium salt of 5-amino-2-(CP (β-D-ribofuranosile)benzo[d]-3H-pyridazine-1,4-dione (10),
sodium salt of 6-amino-2-(β-O-ribofuranosile)benzo[d]-3H-pyridazine-1,4-dione (11),
sodium salt of 5-chlorine-2-(β-D-ribofuranosile)benzo[d]-3H-pyridazine-1,4-dione (12),
disodium salt of 5-hydroxy-2-(β-D-ribofuranosile)benzo[d]-3H-pyridazine-1,4-dione (13),
lithium salt of 5-amino-benzo[d]-3H-pyridazine-1,4-dione (14),
sodium salt of 5-amino-benzo[d]-3H-pyridazine-1,4-dione (15),
potassium salt of 6-amino-benzo[d]-3H-pyridazine-1,4-dione (16),
disodium salt of 5-hydroxy-benzo[d]-3H-pyridazine-1,4-dione (17),
disodium salt of 6-carboxy-benzo[d]-3H-pyridazine-1,4-dione (18).

There were also synthesized and studied derivatives of pyrazine[2,3-d]-6H-pyridazine-5,8-dione of cyclic bioisostere of a derivative of a purine system, in which the pyrazine ring condensed with pyridazinedione, having a general formula:

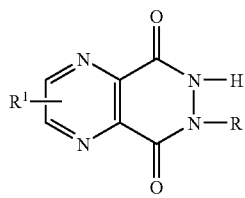

where R=

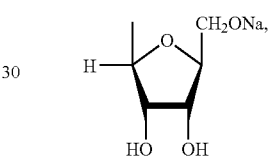

Li, Na, K,
R¹=—NH₂, Br, —OH, —COOH,
in particular:
sodium salt of 7-(β-D-ribofuranosile)pyrazine[2,3—Cl]-6H-pyridazine-5,8-dione (19),
sodium salt of 2-amino-7-(β-D-ribofuranosile)pyrazine[2,3-Cl]-6H-pyridazine-5,8-dione (20),
sodium salt of 3-amino-7-(β-D-ribofuranosile)pyrazine[2,3-d]-6H-pyridazine-5,8-dione (21),
sodium salt of 3-bromine-7-(β-D-ribofuranosile)pyrazine[2,3—Cl]-6H-pyridazine-5,8-dione (22),
disodium salt of 2-hydroxy-7-(β-D-ribofuranosile)pyrazine[2,3—Cl]-6H-pyridazine-5,8-dione (23),
disodium salt of 2-carboxy-7-(β-D-ribofuranosile)pyrazine[2,3-d]-6H-pyridazine-5,8-dione (24),
lithium salt of pyrazine[2,3-d]-6H-pyridazine-5,8-dione (25),
sodium salt of pyrazine[2,3-d]-6H-pyridazine-5,8-dione (26),
potassium salt of 3-bromine-pyrazine[2,3-Cl]-6H-pyridazine-5,8-dione (27),
sodium salt of 2-amino-pyrazine[2,3-d]-6H-pyridazine-5,8-dione (28).

There were also synthesized and studied derivatives of pyrimido[4,5-d]-6H-pyridazine-5,8-dione of cyclic bioisostere of a derivative purine system, in which the pyrimidine ring condensed with a pyridazinedione ring having a general formula:

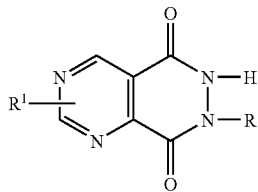

where R=Li, Na, K atom,

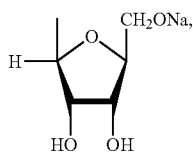

$R^1$=—H, —$NH_2$, —Br, —OH, —COOH,
in particular:
sodium salt of 7-(□-D-ribofuranosile)pyrimido[4,5-d]-6H-pyridazine-5,8-dione (29),
sodium salt of 2-amino-7-(β-D-ribofuranosile)pyrimido[4,5-d]-6H-pyridazine-5,8-dione (30),
sodium salt of 4-amino-7-(β-D-ribofuranosile)pyrimido[4,5-d]-6H-pyridazine-5,8-dione (31),
sodium salt of 2-bromine-7-(β-D-ribofuranosile)pyrimido[4,5-d]-6H-pyridazine-5,8-dione (32),
sodium salt of 4-hydroxy-7-(β-D-ribofuranosile)pyrimido[4,5-d]-6H-pyridazine-5,8-dione (33),
sodium salt of 4-carboxy-7-(β-D-ribofuranosile)pyrimido[4,5-D]-6H-pyridazine-5,8-dione (34),
lithium salt of pyrimido[4,5-d]-6H-pyridazine-5,8-dione (35), 2-amino-pyrimido[4,5-d]-6H-pyridazine-5,8-dione (36),
potassium salt of 4-bromine-pyrimido[4,5-D]-6H-pyridazine-5,8-dione (37).

Compounds 1-8, which are derivatives of pyrido[2,3-d]-6H-pyridazine-5,8-dione, were obtained by condensation of ortho-dicarboxysubstituted pyridines with hydrazine hydrate in an acetic acid medium (Taguchi Hiroshi. "A new fluorometric assay method for quinolinic acid". Analitic Biochemistry, 1983, 131 (1), p. 194-197).

Compounds 9-18, which are derivatives of benzo[d]-3H-pyridazine-1,4-dione (phthalazine dione), were obtained by condensation of ortho-phthalic acid with hydrazine hydrate in an acetic acid medium (Huntress E. H., Stanley L. N., Parker A. S. "The preparation of 3-Aminophtalhydrazide for use in the Demonstration of Chemiluminescence", J, Am. Chem. Soc., 1994, v. 56, p. 241-242).

Compounds 19-28, which are derivatives of pyrazine[2,3-d]-6H-pyridazine-5,8-dione, were obtained by condensation of ortho-dicarboxysubstituted pyrazines with hydrazine hydrate in an acetic acid medium (Zyczynska-Baloniak I., Czajka R., Zinkowska E., "Synthesis of Derivatives of 4-Hydroxypyrazine-[2,3-d]pyridazine-1-one. Polish Journal of Chemistry. 1978, v. 52, p. 2461-2465; Kormendy K., Ruff F. "Pyridazines condensed with a Heteroring. III"., Acta Chimika Hungarika. 1990, 127 (2), p. 253-262).

Compounds 29-37, which are derivatives of pyrimido[4,5-d]-6H-pyridazine-5,8-dione, were obtained by condensation of ortho-dicarboxysubstituted pyrimidines with hydrazine hydrate in an acetic acid medium (Yurugi S., Hieda M. "Studies on the synthesis of N-Heterocyclic Compounds". Chemistry, Pharmaceutic Bull., 1972, v. 20 (7), p 1522-1527. ibid., p. 1513-1521).

The synthesis of these compounds is carried out in a few steps. At the first step the ortho-dicarboxysubstituted heterocycles (pyridine, pyrazine, pyrimidine) or derivatives of phthalic acid ith hydrazine hydrate are condensed in an acetic acid medium:

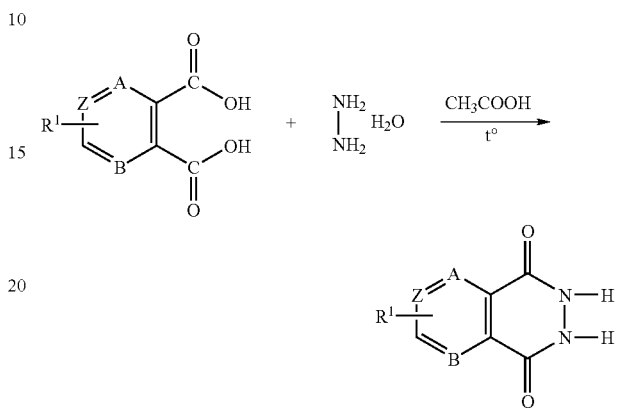

where A, B, Z=—NH=, —CH=, $R^1$=—H, —$NH_2$, Br—, Cl—, OH, —COOH.

At the second step sodium, potassium, lithium salts of respective condensed pyridazinedione are obtained by a reaction with respective ethylate:

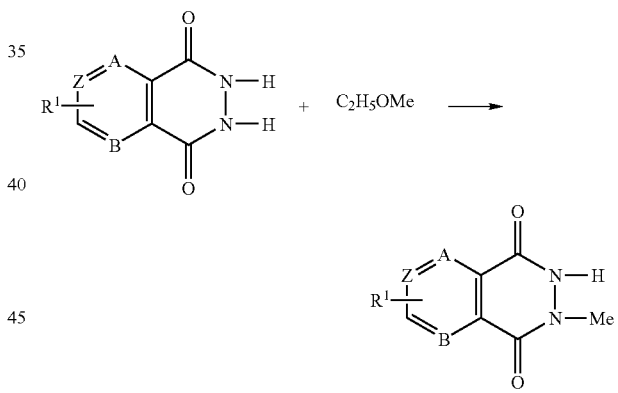

At the final step condensation of an appropriate salt with 1-chlorine-2,3,5-tri-O-toluoyl-β-D-ribifuranose is effected in a medium of anhydrous DMFA in the presence of a catalyst. Used as a catalyst is 15-crown-5 in the case of salt Na or syn-cis, anti-cis-dicyclohexane-18-crown-6 in the case of salt K.

The para-toluoyl protection is removed by sodium salt ethylate.

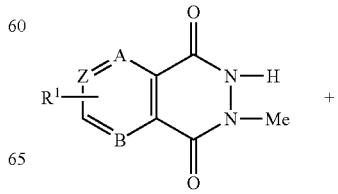

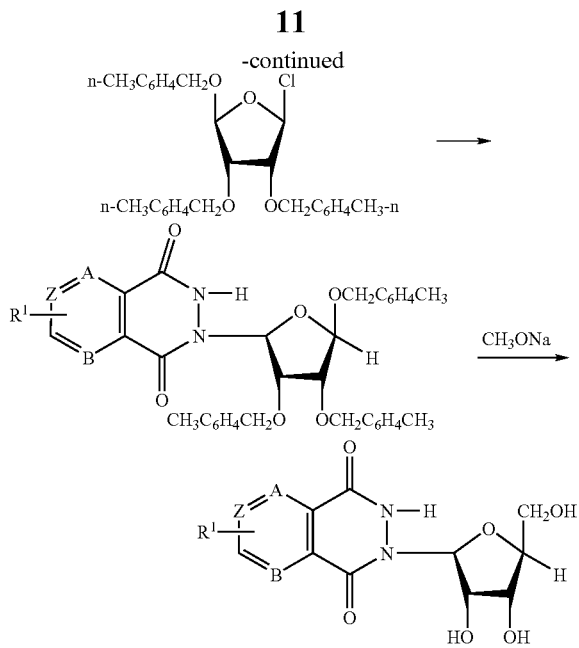

The ribosulation of salts of heterocyclic bases is carried out using a common technique:

Added to a mixture of 1.0 mmol of sodium salt of a heterocyclic base of 1.0 mmol 15-crown-5 in 10.0 ml of dry dimethyl formamide (further DMFA) in an atmosphere of dry argon are drops of 1.0 mmol 1-chlorine-2,3,5-tri-O-toluoyl-β-B-ribofuranose while stirring the mixture. The reaction mass is agitated for 6 to 10 hours at a temperature of 20° C. Then 7.0 ml of 10% solution of $NaHCO_3$ is added and the mixture agitated for 30 minutes at 0° C. 30.0 ml of chloroform is added to the obtained suspension, and the liquid is filtered through Hyflo Super Cel, the organic layer is isolated 10.0 ml of water is used for rinsing, and $Na2_2SO_4$ is dried. The obtained nucleosides are chromatographed on silica gel and $CHCl_3$ is eluated. The yield of nucleosides makes 45-65%.

The removal of the para-toluoyl protection is effected as follows:

Solution of 0.32 mmol nucleazide in a mixture of methanol and dioxane in a ratio of 5:1 is cooled to 0° C., mixed with 0.7 ml of 0.1M solution of sodium methylate in methanol and held in an argon atmosphere for 24 hours at a temperature of 6° C. The reaction mass is neutralized by addition DOWEX 50 ($H^+$) to pH 7.0, the resin is filtered off. The final products are isolated from the filtrate by chromatography on silica gel. The eluent is a mixture of $CHCl_3$ and MeOH in a ratio of 20:1. The yield of the end product makes 66-85%.

Lithium, sodium and potassium salts were obtained by mixing equimolar quantities of heterocyclic compounds with an aqueous solution of appropriate oxyhydroxides. The distillation of water was effected at a reduced pressure without heating according to the well known method of production of alkaline and alkaline-earth salts of aminodihydrophthalazinedione (RU, 2169139, CL).

The structure of the synthesized compounds was confirmed by the data of an elemental analysis using the EA-11-08 ("Carlo Erba") device and chromatography-mass spectrometry on a chromatography-mass spectrometer "Adgilent Technologies".

TABLE 1

The results of chromatography-mass spectrometry study and elemental analysis of compounds 1-37 according to the invention

| Compound No. | (M + H)+ | Found, % | | | Approximate formula | Calculated, % | | |
|---|---|---|---|---|---|---|---|---|
| | | C | H | N | $C_xH_yN_mO_n$Me | C | H | N |
| 1 | 295 | 45.60 | 3.90 | 13.12 | $C_{12}H_{12}N_3O_6Na$ | 45.43 | 3.79 | 13.25 |
| 2 | 310 | 43.51 | 4.08 | 16.69 | $C_{12}H_{13}N_4O_6Na$ | 43.37 | 3.92 | 16.87 |
| 3 | 374 | 36.30 | 2.84 | 10.56 | $C_{12}H_{11}BrN_3O_6Na$ | 36.36 | 2.78 | 10.61 |
| 4 | 306 | 41.20 | 3.10 | 12.07 | $Cu_{11}N_3O_7Na_2$ | 41.03 | 3.13 | 11.97 |
| 5 | 338 | 40.87 | 3.10 | 12.07 | $Cu_{11}N_3O_7Na_2$ | 41.03 | 3.13 | 11.97 |
| 6 | 163 | 49.65 | 2.51 | 24.64 | $C_7H_4N_3O2Li$ | 49.70 | 2.37 | 24.85 |
| 7 | 163 | 45.48 | 2.24 | 22.63 | $C_7H_4N_3O_2Na$ | 45.41 | 2.16 | 22.70 |
| 8 | 163 | 41.87 | 2.12 | 20.78 | $C_7H_4N_3O_2K$ | 41.79 | 1.99 | 20.90 |
| 9 | 294 | 49.51 | 4.23 | 8.72 | $C_{13}H_{13}N_2O_6Na$ | 49.37 | 4.11 | 8.86 |
| 10 | 309 | 47.04 | 4.28 | 12.74 | $C_{13}H_{14}N_3O_6Na$ | 47.13 | 4.23 | 12.69 |
| 11 | 309 | 43130 | 4.44 | 12.47 | $C_{13}H_{14}N_3O_6Na$ | 47.13 | 4.23 | 12.69 |
| 12 | 329 | 44.55 | 3.60 | 8.12 | $C_{13}H_{12}ClN_2O_6Na$ | 47.51 | 3.42 | 7.99 |
| 13 | 309 | 44.18 | 3.56 | 7.70 | $C_{13}H_{12}N_2O_7Na_2$ | 44.07 | 3139 | 7.91 |
| 14 | 177 | 52.60 | 3.12 | 3.13 | $C_8H_6N_3O_2Li$ | 52.46 | 3.28 | 22.95 |
| 15 | 177 | 48.40 | 3.20 | 1.15 | $C_8H_6N_3O_2Na$ | 48.24 | 3.02 | 21.11 |
| 16 | 177 | 44.80 | 2.87 | 9137 | $C_8H_6N_3O_2K$ | 44.65 | 2.79 | 19.53 |
| 17 | 177 | 43.24 | 2.01 | 12.46 | $C_8H_4N_2O_3Na_2$ | 43.24 | 1.80 | 12.61 |
| 18 | 205 | 43136 | 1.78 | 1.14 | $C_9H_4N_2O_4Na_2$ | 43.20 | 1.60 | 11.20 |
| 19 | 296 | 41.70 | 3.52 | 17.80 | $C_{11}H_{11}N_4O_6Na$ | 41.51 | 3.46 | 17.61 |
| 20 | 311 | 39.75 | 3.55 | 21.12 | $C_{11}H_{12}N_5O_6Na$ | 39.60 | 3.60 | 21.73 |
| 21 | 311 | 39.50 | 3.60 | 21.14 | $C_{11}H_{12}N_5O_6Na$ | 39.60 | 3.60 | 21.73 |
| 22 | 375 | 33.40 | 2.47 | 14.15 | $C_{11}H_{10}BrN_4O_6Na$ | 33.25 | 2.52 | 14.11 |
| 23 | 311 | 37.20 | 2.75 | 5.84 | $C_{11}H_{10}N_4O_7Na_2$ | 37.08 | 2.81 | 15.73 |
| 24 | 319 | 39.68 | 2.70 | 15.24 | $C_{12}H_{10}N_4O_8Na_2$ | 39.56 | 2.75 | 15.38 |
| 25 | 164 | 42.47 | 1.59 | 3.07 | $C_6H_3N_4O_2Li$ | 42.35 | 1.76 | 32.94 |
| 26 | 164 | 38.65 | 1.50 | 30.27 | $C_6H_3N_4O_2Na$ | 38.71 | 1.61 | 30.11 |
| 27 | 243 | 25.70 | 0.80 | 9.84 | $C_6H_2BrN_4O_2K$ | 25.62 | 0.71 | 19.93 |
| 28 | 179 | 35.71 | 2.07 | 4.68 | $C_6H_4N_5O_2Na$ | 35.82 | 1.99 | 34.83 |
| 29 | 296 | 41.56 | 3.64 | 7.55 | $C_{11}H_{11}N_4O_6Na$ | 41.51 | 3.46 | 17.61 |
| 30 | 311 | 39.74 | 3.48 | 1.20 | $C_{11}H_{12}N_4O_6Na$ | 39.64 | 3.60 | 21.02 |
| 31 | 311 | 39.60 | 3.72 | 1.13 | $C_{11}H_{12}N_4O_6Na$ | 39.64 | 3.60 | 21.02 |
| 32 | 375 | 33.20 | 2.70 | 4.10 | $C_{11}H_{10}BrN_4O_6Na$ | 33.25 | 2.52 | 14.11 |

TABLE 1-continued

The results of chromatography-mass spectrometry study and elemental analysis of compounds 1-37 according to the invention

| Compound No. | (M + H)+ | Found, % | | | Approximate formula $C_xH_yN_mO_nMe$ | Calculated, % | | |
|---|---|---|---|---|---|---|---|---|
| | | C | H | N | | C | H | N |
| 33 | 311 | 37.00 | 2.94 | 5.57 | $C_{11}H_{10}N_4O_7Na_2$ | 37.08 | 2.81 | 15.73 |
| 34 | 319 | 39.60 | 2.67 | 5.50 | $C_{12}H_{10}N_4O_8Na_2$ | 39.56 | 2.75 | 15.38 |
| 35 | 164 | 42.30 | 1.91 | 3.07 | $C_6H_3N_4O_2Li$ | 42.35 | 1.76 | 32.94 |
| 36 | 179 | 35.70 | 2.12 | 4.90 | $C_6H_4N_5O_2Na$ | 35.82 | 1.99 | 34.83 |
| 37 | 243 | 25.47 | 0.87 | 20.06 | $C_6H_2BrN_4O_2K$ | 25.62 | 0.71 | 19.93 |

The synthesized compounds are colorless or yellowish crystalline substances with a melting point higher than 300° C.

The object of the invention was also attained by developing a pharmaceutical composition according to the invention comprising cyclic bioisosteres of a derivative of a purine system as an active ingredient.

BRIEF DESCRIPTION OF THE DRAWINGS

The invention is further explained by describing the results of the study of biological activity of cyclic bioisosteres of a derivative of a purine system, according to the invention, not limiting their application and within the set of claims with control to the applied drawings, in which:

FIG. 1a illustrates the calibration curves of dependence of the fluorescence intensity of the fluorescence solutions and the cells of mouse NIH 3T3;

FIG. 1b illustrates the calibration curve for determining pHi in the cells of mouse NIH 3T3;

FIG. 2—the dependence of pHi of the cell on pH of the medium;

FIG. 3—the change of the cell pHi at a change in pH of the medium after the administration of the compounds according to the invention;

FIG. 4—the change of the cell pHi at a change in pH of the medium without blood serum after the administration of the compounds according to the invention into the medium;

DESCRIPTION OF THE INVENTION

Figure 3:
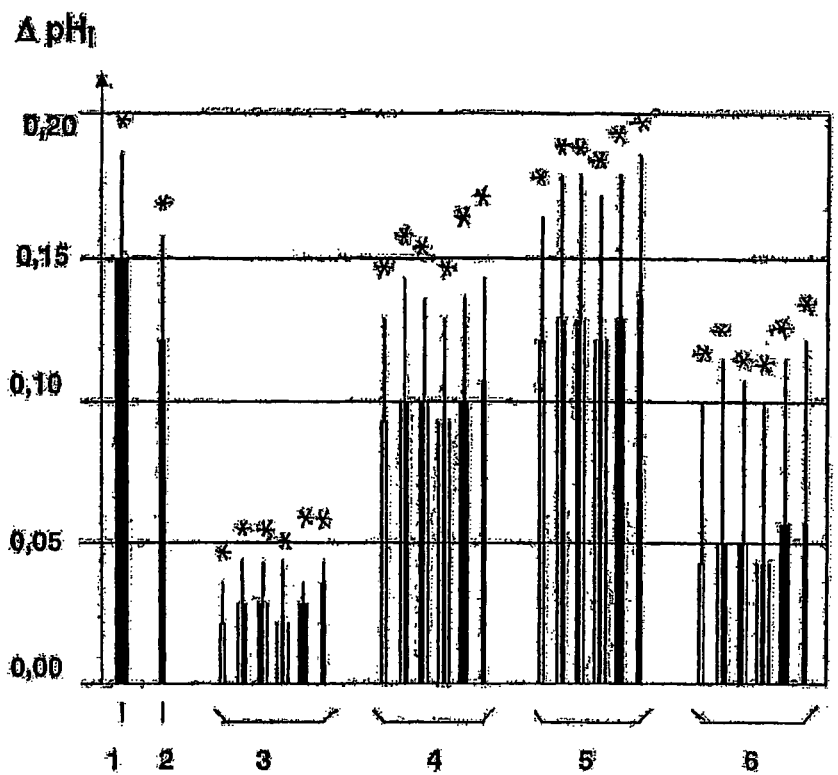
FIG. 3—the dependence of pHi of the cell at a change pH of the medium with blood serum after the administration of the compounds according to the invention into the medium.

From the published data it is known that cyclic hydrazides are either not a subject to polarographic reduction or are reduced in a concentrated acid or alkaline solutions at a sufficiently high potential of the half-wave $E_{1/2}>1.0$ V (Seo E., Kuwana T. "Polarography of cyclic Hydrazides", J. Electroanal. Chem., 1963, v. 6, p. 417-418; Lund H. "Polarographic and electropreparative reduction of 1(2H)-phthalazines, 2,3-dihydro-1,4 phthalazindiones and related compounds", Coll. Czechoslow. Chem. Com., 1965, v. 30. p. 4237-4249).

However, the inventors have found that compounds 1-37 according to the invention being salts of alkali metals of cyclic hydrazides are liable to electrochemical reduction at a value of the half-wave potential $E_{1/2}$ from minus 0.09 V to minus 0.2 V.

For comparison, we may give an example of electrochemical reduction of coenzyme $NAD^+$ effected at $E_{1/2}=-0.32$ V, in which the molecule $NAD^+$ receives two electrons and one proton, the second proton remaining in the medium:

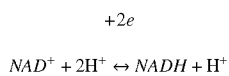

$$NAD^+ + 2H^+ \overset{+2e}{\leftrightarrow} NADH + H^+$$

In flavin coenzymes $FAD^+$, in which an isoalloxazine ring is an active part of the molecule, the reduction at the potential $E_{1/2}=-0.05$ V very often results in connection of two protons and two electrons simultaneously.

The reduced forms of these coenzymes NADH and FADH transport hydrogen and electrons to the respiratory chain of mitochondrions or others energy distributing membranes.

The respiratory chain of the mitochondrions includes cytochromes b, $c_1$, c, a and $a_3$ in an order of rising the magnitude of their redox potential set under conditions of pH 7.0, t=25° C.:

$$b(Fe^{3+})E_{1/2}=+0.07 \text{ V}, c1(Fe^{3+})E_{1/2}=+0.23 \text{ V},$$

$$c(Fe^{3+})(Fe3+)E_{1/2}=+0.25 \text{ V},$$

$$a(Fe^{3+})E_{1/2}=+0.29 \text{ V}, a_3(Fe_{3+})E_{1/2}=+0.55 \text{ V}$$

that play an important role in the process of tissue respiration.

The cytochrome is a terminal section of the respiratory chain—cytochrome oxydase, which performs oxidation of the cytochrome with formation of water. The elementary act is two-electron reduction of one atom of oxygen, when each molecule of oxygen interacts with two electrotransport circuits. In the process of transport of each pairs of electrons, up to 6 protons can collect in interrnitochondrial space. A change of the ratio in the amount of protons and electrons can result in disorder of the tissue respiration.

The inventors have found that each molecule of compounds 1-37 according to the invention is capable of penetrating into the endocellular space and, having redox potential comparable to the potentials of the electrochemical reduction of the above processes, can irreversibly attract up to 4 electrons and protons, thereby promoting the intensifications of the processes of tissue respiration and appreciable decrease of a metabolic endocellular acidosis.

1. Electrochemical Activity of the Compounds According to the Invention.

The electrochemical activity of the compounds according to the invention has been studied.

Subjected to study were aqueous solutions of compounds 1, 5, 7, 10, 15, 18, 23, 25, 27, 33, 35, 36 according to the invention with an initial concentration of $1 \cdot 10^{-2}$ mol/l and, for comparison, a solution of the «dimephosphon» drug of the same concentration was used.

The study was carried out on a general-purpose polarograph PU-1 with a two-coordinate recorder of the "LKD" type using a three-electrode thermostatically controlled polarographic cell and mercury dripping electrode (MDE) with forced separation of the drop and a dropping period of 0.5 second. A platinum wire was used as an auxiliary electrode and a saturated calomel electrode (SCE) was used as a control electrode.

2.0% solutions of sodium chloride having pH 7.0, 7.2, 7.4, 7.6 were used as a background; the pH values of the background solution were corrected by a solution of sodium hydroxide. The polarographic cell was filled with 5.0 ml of the background solution and for 5 minutes was purged with nitrogen for removing the dissolved oxygen. Then 0.5 ml of solution of the studied substance was added to the background solution, and the polarogram was recorded as a polarographic wave. The concentration of the compounds in the polarographic cell was $9 \cdot 10^{-4}$ M.

The pH was measured on the pH-meter with an accuracy of ±0.05 pH units. The polarographic measurements were carried out at a temperature of 37° C. The recording of polarograms of the investigated materials was effected under conditions of DC current at a scanning rate of the potential 10.0 mV/s with a active scanning stroke from a potential 0 to −0.5 V and sweep retrace from a −0.5 V to 0. The electric-current sensitivity was 5.0 mkA. The scale by the coordinate of the potentials was 50.0 mV/cm. The values of potentials of the half-wave $E_{1/2}$ of the investigated materials are given with respect to the SCE potential.

The polarogram parameters such as a limiting current $i_{lim}$ and $E_{1/2}$ were determined by the graphic method. The number of electrons participating in the reaction was calculated on the basis of the analysis of the polarographic wave using the Geirovsky-Ilkovich equation.

The average values of the parameters of the polarographic wave of the investigated materials at a forward recording trace are presented in Table 2.

TABLE 2

Parameters of polarograms of the compounds

| Compound | | pH | | | |
|---|---|---|---|---|---|
| No. | | 7.0 | 7.2 | 7.4 | 7.6 |
| 1, 5, 7 | i, mkA | 0.26 ± 0.04 | 0.31 ± 0.02 | 0.27 ± 0.03 | 0.30 ± 0.01 |
| - « - | $-E_{1/2}$, V | 0.11 ± 0.02 | 0.11 ± 0.03 | 0.105 ± 0.01 | 0.105 ± 0.02 |
| 10, 15, 18 | i, mkA | 0.23 ± 0.03 | 0.30 ± 0.01 | 0.29 ± 0.02 | 0.31 ± 0.02 |
| - « - | $-E_{1/2}$, V | 0.092 ± 0.02 | 0.09 ± 0.01 | 0.092 ± 0.02 | 0.09 ± 0.01 |
| 23, 25, 27 | i, mkA | 0.32 ± 0.03 | 0.33 ± 0.04 | 0.34 ± 0.03 | 0.34 ± 0.02 |
| - « - | $-E_{1/2}$, V | 0.16 ± 0.02 | 0.19 ± 0.02 | 0.175 ± 0.01 | 0.16 ± 0.015 |
| 33, 35, 36 | i, mkA | 0.30 ± 0.05 | 0.26 ± 0.02 | 0.30 ± 0.03 | 0.30 ± 0.02 |
| - « - | $-E1_{/2}$, V | 0.08 ± 0.02 | 0.085 ± 0.015 | 0.085 ± 0.02 | 0.09 ± 0.02 |
| Dimesphosphon | i, mkA | 0.10 ± 0.03 | 0.12 ± 0.03 | 0.11 ± 0.02 | 0.11 ± 0.02 |
| - « - | $-E_{1/2}$, V | 0.175 ± 0.01 | 0.17 ± 0.02 | 0.18 ± 0.01 | 0.18 ± 0.01 |

During experiments it was noticed that, compared to the values of the forward stroke, with a record of the polarograms of reverse stroke the value of the half-wave potential had a higher positive potential by 25.0 mV for compounds 1, 5, 7, by 30.0 mV for compounds 10, 15, 18, by 20.0 mV for compounds 23, 25, 27, by 27.0 mV for compounds 33, 35, 26, and by 50.0 mV for the dimephosphon drug.

The given data testify on irreversibility of the process of electrochemical reduction of these compounds.

The calculation of the number of electrons participating in the reduction reaction was effected using the Geirovsky-Ilkovich equation:

$$E = E_{1/2} - \frac{2.3\,RT}{nF} lg \frac{i}{i_{lim} - i},$$

where n is the number of electrons,
i is the current value of the wave current, mkA $I_{lim}$ is the value of the limiting wave current, mkA,
F is the Faraday number equal to 96500K,
R is the universal gas constant equal to 8.31 Jole/mol·K
T is the temperature, K,
E, $E_{1/2}$ are the potentials, V.

As a result of these calculation, it has been found that during the reduction:
for compounds 1, 5, 7 the number of electrons is equal to 3.72,
for compounds 10, 15, 18—4.09,
for compounds 23, 25, 27—3.72,
for compounds 33, 35, 36—3.5,
for dimephosphone—1.6, i.e. during the reduction of the investigated compounds according to the invention 4 electrons are consumed, and during the reduction of dimephosphone—2 electrons, so we may conclude that compared to dimephosphon the compounds according to the invention manifest higher ability for irreversible attachment of electrons.

The biological activity of the compounds according to the invention was studied.

2. Effect of the Compounds According to the Invention on pH of a Cell

Many pH adjusting are known including $Na^+/H^+$ interchangers located in the plasmatic membrane, Na-dependent and Na-independent $HCO_3^-Cl^-$ interchangers increasing the $pH_i$ of the cytosol cell, $Cl^-/HCO_3^-$ interchangers decreasing the $pH_i$ of the cytosol cell, carriers of complexes of ions $Na^+$ with monocarboxylates, proton pumps $H^+$—ATF-ases, etc. (Ganz M. B. et all. "Argininvasopression enchangers of pH, regulation in the presence of $HCO_3^-$ by stimulating three acid-base transport systems", Nature, 1989, v. 337, p. 648-651) are known.

In view of similarity of biochemical mechanisms of various types of cells, we may come to a conclusion that if a certain agent changes the endocellular $pH_i$ in a definite type of cells, therefore, in view of similarity of the mechanisms of regulation of $pH_i$, the same agent will change the $pH_i$ in other types of cells. In particular, if the compounds according to the invention result in a change of $pH_i$ of fibroblasts, they can affect the $pH_i$ of macrophages and neutrophils.

It is well known that the activation of macrophages is associated with production and extrusion of protons, with activation of the systems of transport of protons from a cell by means of proton pumps, $Na^+/H^+$ interchangers, systems of transport of sodium bicarbonate (Rogachev B., Hausmann M. J., Julzari R., Weiler H., Holmes C., Falct D., Chaimovitz C., Douvdevani A. "Effect of bicarbonate-based dialysis solution on intracellular pH ($pH_i$) and TNF-alpha production by peritoneal macrophages, Perit. Dial. Int., 1997, November-December, 17 (6), p. 543-553; Bidani A., Heming T. A. "Effect of concanavalin A on $Na^+$-dependent and $Na^+$-independent mechanism for $H^+$ extrusion in alveolar macrophages", Lung., 1998, 176 (1), p. 25-31; Swallow C. J., Grinstein S., Sudsbury R. A., Rotstein O. D. "Relative roles of $Na^+/H^+$ exchange and vacuolar-type $H^+$ ATPases in regulating cytoplasmic pH and Function in murine peritoneal macrophages", J. Cell. Physiol., 1993, 157 (3), p. 453-460)

For example, the activation of the mechanisms of increasing $pH_i$ of cell cytosol, for example, $Na^+/H^+$ antiporter is necessary for increasing the activity of neutrophils and their microbicidal activity, because a decrease of the cytosol pH blocks the functional activity of neutrophils.

2.1. Effect of the Compounds According to the Invention on $pH_i$ of Fibroblasts The effect of the compounds according to the invention on the endocellular pH, embryonic fibroblasts of mouse NIH-3T3 supplied by the All-Russian Collection of Cellular Cultures of the Institute of Cytology of the Russian Academy of Sciences St. Petersburg was investigated. The cells were grown in the DMEM (Sigma) medium containing 2.2 g/l of sodium bicarbonate with addition of 80.0 mkg/ml of gentamicin and 10.0% embryonal veal serum at a temperature of 37° C. in an atmosphere containing 5.0% of carbon dioxide. For these experiments use was also made of a medium buffer with 5.0 mM of HEPES and 15.0 mM of sodium bicarbonate without serum or with addition of 5.0% serum. The cells were calculated with the help of a hemocytometer. A share of the dead cells was determined by colouring trypan blue.

The measurements of the endocellular $pH_i$ were carried out with the help of colorants FDA (Sigma) and BCECF-AM (Calbiochem) on a microspectrofluorimeter by a standard technique (Koshevoy Yu. V., Akatov V. S., Grobova M. E. Microspectrofluorimeter for measuring endocellular pH (micro pH)". Devices and equipment for studies in the field of physical-and-chemical biology and biotechnology. Pushchino, 1990. P. 8-14).

The cells at a temperature of 37° C. were colored within 5 minutes with 5.0 mkM PDA that before the colouring was prepared from a 10.0 mM solution in acetone by dilution for 30 minutes in a phosphatic buffer to 0.1 mM or 2.0 mkM 1.0 mM solution BCECF-AM in DMSO.

The two-wave method of determining $pH_i$ was used based on the ratio intensities of fluorescence of the cells on two wavelengths (Akatov V. S. et all), "Endocellular pH and substrate dependence of proliferation of fibroblasts of Chinese hamster, Cytology, 1991, 33 (7), p. 86-94). The fluorescence was excited by light at $\lambda=490$ nm, the emission was recorded simultaneously with two photomultipliers on wavelengths $\lambda=535$ nm and $\lambda=570$ nm. The K-ratio of the fluorescence on two wavelengths was determined with a deduction of the background fluorescence of the medium near the investigated cells for 40-60 individual cells, which are then averaged taking into account the measurement error. A thermostatically controlled table was used that allowed measurements to be conducted at a temperature of 37° C. An account was taken for the photodynamic damage of the pigmented cells during long-time continuous illumination by excited light. The readings were taken from a section of the preparation exposed to light for not more than 5 minutes.

Calibration of Instruments

The calibration curves for determining the absolute $pH_i$ values by magnitude K were constructed using the Thomas technique (Thomas J. A., Bushbaum R. N., Zimniak A. w Racker E. "Intracellular pH measurements in Ehrlich ascites tumor cells utilizing spectroscopic probe generated in situ", Biochemistry, 1979, v. 18, p. 2210-2218), for which case the pigmented cells treated for 5-10 minutes with carboxyacidic nigericyn (Calbiochem) at a concentration of 5-10 mkg/ml was placed in a solution with a high content of potassium—130 mM KCl, 1.0 mM $MgCl_2$, 20.0 mM of HEPES) and with pH values from 6.2 to 7.6. The K values were measured in the media with different pH assuming that $pH_i$ of the cells equals to the pH of the medium due to the action of nigericyn, which exchanges potassium ions for protons and at a high content of potassium in the medium counterbalances the pH of the medium and cells. Calibration curves were used based on the fluorescence of same medium with addition of 5.0 mkM of fluorescence or BCECF were used to the control the stability of the of the instrument readings.

The correctness of the technique was confirmed in the experiments on measurements of pH values of cells treated with protonofor monencine raising pH of the cells due to replacement of sodium ions by protons, and by determining the dependence of the change of $pH_i$ on the change of the pH of the medium. The pH value of the medium ($pH_0$) was set in the DMEM medium without serum containing 5 mM of HEPES and 15 mM of sodium bicarbonate, by titration with HCl or KOH. The incubation time of the cells in the medium with a given pH value was effected for at least 10 minutes, and this is a sufficient time for setting balance of the $pH_i$ of the cells with the medium pH (Li J., Eastman A. "Apoptosis in an interleukin-2-depended cytotoxic T-lymphocyte cell line is associated with intracellular acidification", J. Biol. Chem., 1995, v. 270. p. 3203-3211).

Shown in the graph of FIG. 1*a* are the calibrating dependencies of value K or the ratio of intensities of fluorescence at 530 and 570 nM of fluorescent solutions having pH in a range of 6.4-7.5 (curves 1), and cells of mouse NIH 3T3, loaded with FDA and placed in solutions containing KCl, nigericine and buffer HEPES in a range of pH 6.5 to 7.5 (curve 2). As it is seen from the graphs, the calibration dependencies for cells NIH 3T3 are displaced to the right for 0.1 pH unit relative to the calibration curves of the fluorescent solutions. The constancy of calibration of the instrument using the fluorescence solutions, was supervised in the course of measurements of the effect of the compounds according to the invention on the $pH_i$ and recalculation of the K values in $pH_i$ for cells loaded with FDA is carried out under curve 2. Within one day the calibration was kept with an accuracy of ±0.05 units $pH_i$ and within a month of work with an accuracy of ±0.1 unit pH.

On the graph of FIG. 16 calibration for cells loaded with pigment BCECF-AM placed in a solution with KCl, nigericine and buffer HEPES (pH 6.5-7.5) is shown. This calibration dependence was used for determining the $pH_i$ in cells loaded with BCECF-AM. In so doing different pigments are used since it is well known that colored FDA can show pH values of not only cytosol but also mitochondrions while the BCECF-AM is an $pH_i$ indicator, basically, cytosol.

2.1.1. Estimation of Dependence of $pH_i$ of Fibroblasts on pH of Exocellular Medium.

The dependence of $pH_i$ of fibroblasts on pH of the medium was studied for estimation of possible effect of the compounds according to the invention due to an increase of $pH_i$ of the cell of the medium.

The cells were colored by pigment BCECF-AM and $pH_i$ was measured 10 minutes after incubation in the medium with an appropriate pH value.

The graph in FIG. 2 illustrates the dependence of $pH_i$ of fibroblasts of mice NIH 3T3 on the pH of the medium. The results of the study have shown that in the physiological range of pH from 6.9-7.0 to 7.4-7.5 the optimum for the cellular of processes the $pH_i$ is maintained at a constant level. As the pH of the medium to a value of 6.9, $pH_i$ drops down, and the cells are not capable of maintaining the $pH_i$ level in the optimum physiological range.

We have also found that at pH of the medium above the optimum physiological range the value of $pH_i$ does not increase but drops down, and this may be explained by inclusion of certain adaptive mechanisms of the cell. Only at sublethal for cells pH values of the medium of about 8.5 or more, the $pH_i$ in a cell rises up to optimum values and higher ($pH_i$ 6.9 to 7.1).

It is well known that blood serum has growth factors, which can to rise $pH_i$. To estimate the condition and possibilities of the instrument, and for comparison with the action of the preparation, the effect of serum on the $pH_i$ value of the fibroblasts in a suspension was estimated. For this purpose, the $pH_i$ was measured before addition and 20 minutes after addition of 10% serum. It has been found that after addition of serum the $pH_i$ increased by 0.15 units. In the total of 11 experiments the $pH_i$ value of the fibroblasts in a suspension with serum made 6.94±0.01 (12 measurements), and without serum 6.85±0.01 (14 measurements). The measurements were made using FDA and BCECF-AM.

As it is known to those skilled in the art, $On^+$—ionophore monencine initiates strong enter of protons into $Na^+$ cells and output of protons therefrom and this results in an increase of $pH_i$. For example, in the cells of mice NSO and NIH-3T3 the administration of 1-5 mkM of monensine within 15-20 minutes initiates an increase of $pH_i$ for 0.2 unit (Solovieva M. E., Akatov V. S., Leshchenko V. V., Kudryavtsev V. A. "The mechanism of destruction of cells of myeloma NS/O in culture". Proceeding of the Russian Academy of Sciences, 1998, 2, p. 194-189) and this is in good agreement with the literature data (Zhu W.-H., Loh T.-T. "Effects of Na+/H+ antiport and intracellular pH in the regulation of HL-60 cell apoptosis", Biochim. Biophys. Acta, 1995, v. 1269, p. 122-128). On checking this result it has been found that the addition of 10 mkM of monensine into the medium with serum initiates a rise of $pH_i$ by 0.12 pH unit.

The obtained results on the effect of serum and monensine on $pH_i$ have proved the reliability of the instrument readings and serve as an landmark for comparison of the effects called by the compounds according to the invention.

2.1.2. Study of the Action of the Compounds According to the Invention on Phi of Fibroblasts.

The graph in FIG. 3 illustrates the results of the study of the change of the NIH 3T3 fibroblasts in a growth medium DME containing 10.0% blood serum, (field 1) 20 minutes after addition to this medium of a compound from compounds 7, 15, 18, 23, 35, 36 in different concentrations: 0.02 mkg/ml (field 3), 0.2 mkg/ml (field 4), 2.0 mkg/ml (field 5), 20.0 mkg/ml (field 6), from left to right, respectively; of value $\Delta pH_i$ at introduction into the medium of compounds 7, 15, 18, 23, 35, 36 and, for comparison, at introduction into the medium of 10 mkM of monensine (field 2).

It has been found that the compounds according to the invention at a concentration of 0.02 mkg/ml did not increase $pH_i$. At a concentration of 20.0 mkg/ml the compounds cause a reliable increase of the growth was on the average 0.05 unit $pH_i$ but was not reliably distinct from zero because of a wide scatter of the results. At a concentration of 0.2 and 2.0 mkg/ml the compounds cause a reliable increase of $pH_i$ the cell cytosol on the average by 0.10 and 0.12 unit of $pH_i$, respectively, similar to the effect observed when adding serum or monensine.

Figure 4:
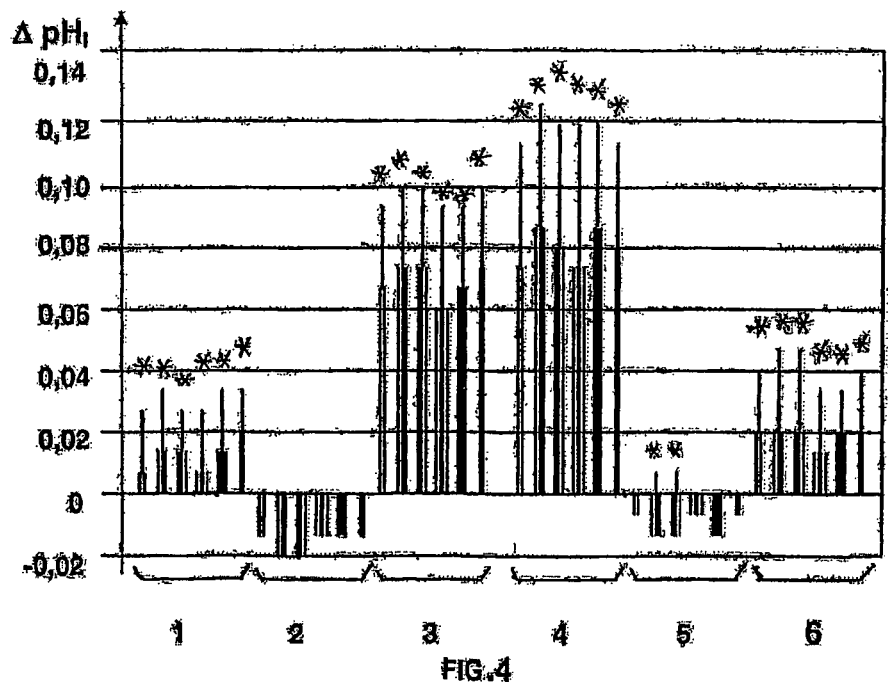
FIG. 4—the dependence of the cell pHi at a change of pH of the medium with no compounds according to the invention in the medium.

On the chart of FIG. 4 there are presented the results of the study of the change of $pH_i$ of the cells 20 minutes after addition of the same compounds at a concentration of 0.02 mkg/ml (field 1 of the chart), 0.2 mkg/ml (field 2), 2.0 mkg/ml (field 3), 20.0 mkg/ml (field 4), 200 mkg/ml (field 5) and 1000 mkg/ml (field 6), respectively, from left to right, during the introduction of a compound 7, 15, 18, 23, 35, 36 into medium DME without blood serum, in the absence of growth factors soluble in the medium, cytokines. Under these conditions the investigated materials at a concentration of 2.0 and 20.0 mkg/ml reliably raised $pH_i$ on the average by 0.08 unit $pH_i$, and no effect was found on the $pH_i$ of the compounds according to the invention at a concentration of 0.02, 0.2, 200 and 1000 mkg/ml.

Figure 5:
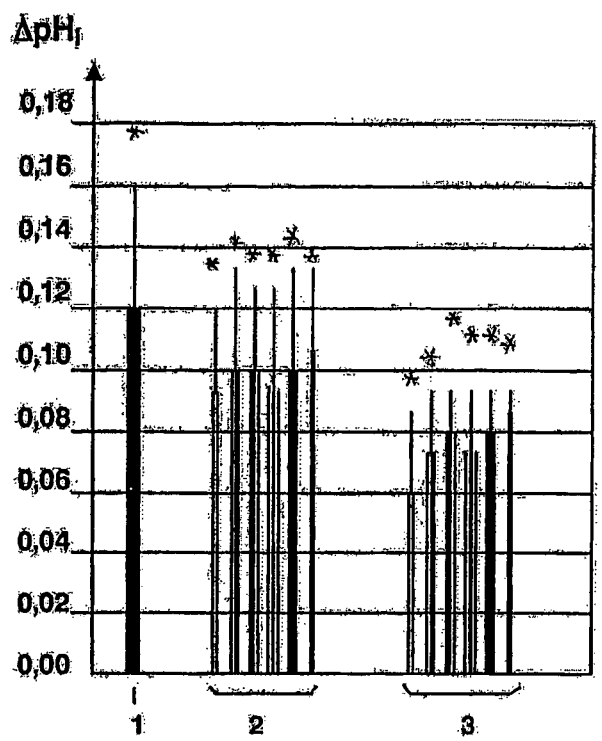
FIG. 5—the change of pH, of fibroplasts in an attached spread state after the administration of the compounds according to the invention into the medium.

Shown on the chart of FIG. 5 are the results of the study of the effect of introduction of the compounds according to the invention into the medium at a concentration of 2.0 mkg/ml (field 2) and 20.0 mkg/ml (field 3) on the $pH_i$ of fibroblasts in an attached spread state in field 2 and 3, a change from left to right change, respectively, for compounds 7, 15, 18, 23, 35, 36, and, for comparison, the effect of introduction of 10.0 mkM of monensine (field 1). This study was conducted, because under conditions in vivo fibroblasts are usually attached and spread on the tissue matrix elements. It has been found that in this case the investigated materials at a concentration of 2.0 and 20.0 mkg/ml also result in a reliable rise of $pH_i$ on the average by 0.10 and 0.07 unit $pH_i$ similarly to that observed under the action of monensine.

Conclusions

The obtained results have shown that in a medium with blood serum in the presence of the growth factors and cytokines, compounds 7, 15, 18, 23, 35, 36 according to the invention cause a reliable increase of $pH_i$ of cytosol of embryonic fibroblasts of mice of line NIH 3T3: at a concentration of 0.2 mkg/ml—on the average 0.1 unit pH and at a concentration of 2.0 mkg/ml—on the average of 0.12 unit pH and do not initiate a change of pH at concentrations of 0.02 and 20.0 mkg/ml. The growth of $pH_i$ caused by the administration of the compounds according to the invention is comparable to that observed under an effect of the growth factors of blood serum or ionophore monensine—a known agent causing an increase of $pH_i$ of cytosol.

In a medium without blood serum, the compounds according to the invention at a concentration of 2.0 mkg/ml and at a concentration of 20.0 mkg/ml reliably increased the $pH_i$ of fibroblasts of the mouse of line NIH 3T3 on the average by 0.08 unit pH and no reliable effect on $pH_i$ of the compounds according to the invention was found at concentrations 0.02, 0.20, 200 and 1000 mkg/ml.

The compounds according to the invention at a concentration of 2.0 mkg/ml and at a concentration of 20.0 mkg/ml reliably induced an increase of $pH_i$ of cytosol of the line NIH 3T3 mouse fibroblasts attached to an exocellular matrix, on the average by 0.08 unit pH.

All compounds according to the invention at a concentration of at least 2.0 mkg/ml did not cause changes of pH of the medium with blood serum, and their effect on the $pH_i$ of the fibroblasts is not connected with the change of the medium pH caused by them.

The addition of the compounds according to the invention at a concentration of to 2.0 mkg/ml to a medium with 10.0% of serum at an initial pH of the medium of 7.2±0.1 did not cause an increase of pH of the medium at measurements with an accuracy of up to 0.03 unit pH.

Thus, it has been shown that the compounds according to the invention at concentrations of 0.2, 2.0, 20 mkg/ml cause increase of $pH_i$ of cytosol of fibroblasts both in the attached state and in a suspension, irrespective of the growth factors and cytokines of blood serum in the medium. The magnitude of rise of $pH_i$ generated by these compounds is comparable to the magnitude observed at the action of the growth factors of serum or monensine ionophore, i.e. a well known agent increasing the cytoplasm pH.

3. Interaction of the Compounds According to the Invention with Adenosine-Sensitive Receptors.

During the comparative analysis of the chemical structure of the compounds according to the invention or the derivatives of benzo[d]pyridazinedione, pyrido[2,3-d]pyridazinedione, pyrazine[2,32]pyridazinedione and pyrimido[4,5-d]pyridazinedione assumptions were made about cyclic isosterism of these compounds and other derivatives of the purine system: adenine, guanine, hypoxanthine. The analysis of their structure allows one to make a conclusion that all the above listed derivatives are condensed heterocyclic ring compounds having similar distribution of electron density. The Stewart-Brigleb models and the above-described reactions ribolization of the compounds according to the invention convincingly prove that β-d-ribofuranose fragment can join the nitrogen atom of pyridazinedione fragment of any of the listed heterocycles. The obtained information allowed us to assume that the compounds according to the invention may feature a biological activity similar to that of the derivatives of the purine of system, in particular, can have isotropy to adenosine-sensitive receptors, and the available differences in the structure and distribution of the π-electron cloud of molecules allow us to predict the presence of additional biological activity, which is absent in derivatives of the purine system: adenine, guanine, hypoxanthine.

3.1. Interaction of the Compounds According to the Invention with Adenosine-Sensitive Receptors of Thrombocytes.

One of the examples confirming probable similarity of the structure of the compounds according to the invention with the structure of adenosine is a decrease of aggregation of thrombocytes.

At present, there is known an insignificant amount of medicinal preparations, such as acetosalicylic acid, dipiridamol, indobufen, pentoxyphiline, clopidogel and ticlopidineis used as means for depressing the aggregation of trobocites and improving microcirculation. Note that their efficiency is not satisfactory in all cases of application, and their use is accompanied by side effects due to the ulcerogenic and hepatotoxic action, allergic properties and other undesirable effects.

The compounds according to the invention were studied for the effect of aggregation of thrombocytes induced by a preliminary introduction of a solution of an aggregation inductor with a competing introduction of the compounds according to the invention.

The aggregation of thrombocytes was studied by the Born method based on determination of the changes in the optical density of plasma enriched with thrombocytes after its incubation with an aggregation inductor.

Adenozinediphosphoric acid (ADP) was selected as an aggregation inductor, which in fact is an aggregation generator. Use was made of a sample (registration number 885) of the Sigma Diagnostics Company (USA) in final concentration of $10^{-5}$ M.

The ADP released from the thrombocytes at the initial step of cellular homeostasis initiates formation of an irreversible conglomerate of platelets and is one of integrators of different ways of increasing the amount of thrombocyte platelet aggregates: a phosphoinositol way, release of calcium, cyclic mononucleotides, activation of calmodulin and other ways.

The experiments were carried out on male rabbits of the "Chinchilla" breed having a mass of 2.7±0.3 kg. 18-24 hours prior to the experiment they were deprived of feed while preserving free access to water.

To obtain plasma enriched with thrombocytes, blood was taken from a cut of a marginal vein of the rabbit ear, the sample was stabilized with 3.8% of sodium citrate solution in a ratio of 9:1 and centrifuged at 200 g (1000 rev/min) for 10 minutes. The top supernatant layer enriched with thrombocytes was transferred by an automatic dropper into a silicone test tube and kept at 37° C. The plasma enriched with thrombocytes contained, on the average, 3×108 blood platelets in 1 liter. If this content exceeded the specified 3×108 blood platelets in 1 liter, this sample was diluted to the necessary concentration with plasma deprived of thrombocytes, which was obtained by centrifuging blood at 650 g during 10 minutes.

The measurements of the optical density of the samples were made on two-channel aggregometer of the "Chronolog" Company (USA). A flask containing 490 mkl of plasma rich with thrombocytes was placed in a device, into which a magnetic agitator covered with Teflon was lowered. The index of maximum amplitude of aggregation (MA) in percent of a fall of the plasma optical density under effect of the aggregation inductor was recorded. The control index MA of plasma was compared with the MA of plasma incubated for 3 minutes with different concentrations of the compounds: from $10^{-3}$ to $10^{-7}$ in vitro experiments or with plasma obtained 15, 30, 60 and 120 minutes after intravenous administration of different doses of the compounds in vivo experiments.

The process of aggregation of thrombocytes was recorded with the help of a computer; on the monitor screen the there were depicted curves reflecting changes of the optical density of the plasma enriched which was taken as a standard 100% compared to the optical density of the non-thrombocyte plasma taken for 0% content of thrombocytes.

3.1.1. The In Vitro Studies.

Under in vitro conditions a flask was filled with blood plasma enriched with thrombocytes, to which an aggregation inductor ADP was added at a concentration of $10^{-5}$ M, incubated for 3 minutes, and then the compounds according to the invention were introduced directly into the flask. Their action by aggregation of thrombocytes was studied after 3-minute incubation in a wide range of concentrations from $10^{-3}$ to $10^{-7}$ M to minimum concentration of $10^{-7}$M not inducing no effect of suppressing the aggregation. The results of thus study are given in Table 3.

ing to the invention has manifested approximately the same degree of suppression of the aggregation.

A lower concentration of the compounds in the order of 10 to 6 M reduced the aggregation in a significantly shorter range—from 3.4% to 17.2%. In a concentration of $10^{-7}$ M the action of the compounds stopped.

The data obtained in vitro indicate to a high antiaggregative capability of the compounds according to the invention in a range of concentration from $10^{-3}$ M to $10^{-5}$M.

3.1.2. Investigations In Vivo.

The antiaggregative capability of compounds 2, 15, 21, 37, according to the invention was tested in experiments in vivo. Introduced to the test animals intravenously were an aggregation inductor ADP at a concentration of $10^{-5}$ M was and

TABLE 3

Effect of the compounds according to the invention on the ADF-induced aggregation of thrombocytes o the rabbits in vitro

| | MA - fall of optical density of plasma, % to the standard, at a concentration of compounds | | | | | |
|---|---|---|---|---|---|---|
| | $10^{-3}$ M | | $10^{-4}$ M | | $10^{-5}$ M | |
| Compound | Control | Experience | Control | Experience | Control | Experience |
| 2 | 60.8 ± 3.4 | 51.4 ± 2.7* | 60.0 ± 2.1 | 50.4 ± 1.7* | 52.5 ± 2.1 | 48.2 ± 1.0* |
| 4 | - « - | 49.2 ± 2.3* | - « - | 50.2 ± 2.0* | - « - | 46.2 ± 3.1* |
| 6 | - « - | 50.0 ± 1.9* | - « - | 53.3 ± 2.2* | - « - | 47.4 ± 2.0* |
| 9 | - « - | 47.3 ± 2.0* | - « - | 53.1 ± 1.8* | - « - | 41.4 ± 3.4* |
| 10 | - « - | 46.2 ± 2.7* | - « - | 48.7 ± 2.4* | - « - | 40.2 ± 4.0* |
| 15 | - « - | 44.8 ± 2.8* | - « - | 46.3 ± 1.7* | - « - | 39.8 ± 3.1* |
| 21 | - « - | 47.1 ± 3.0* | - « - | 49.2 ± 2.1* | - « - | 41.8 ± 2.4* |
| 25 | - « - | 48.2 ± 2.9* | - « - | 48.6 ± 2.0* | - « - | 43.4 ± 3.2* |
| 28 | - « - | 49.7 ± 2.2* | - « - | 48.9 ± 2.4* | - « - | 44.2 ± 2.7* |
| 31 | - « - | 44.9 ± 2.3* | - « - | 46.7 ± 2.2* | - « - | 39.9 ± 2.1* |
| 36 | - « - | 45.8 ± 2.3* | - « - | 46.9 ± 2.4* | - « - | 40.1 ± 2.0* |
| 37 | - « - | 46.9 ± 2.7* | - « - | 47.1 ± 2.0* | - « - | 40.6 ± 1.7* |

| | MA - drop of optical density, % compared to control, at a concentration of compounds | | | |
|---|---|---|---|---|
| | $10^{-6}$ M | | $10^{-7}$ M | |
| Compound | Control | Experience | Control | Experience |
| 2 | 52.8 ± 1.8 | 50.1 ± 2.0 | 51.5 ± 2.1 | 50.8 ± 2.2 |
| 4 | - « - | 50.6 ± 3.1 | - « - | 49.9 ± 3.4 |
| 6 | - « - | 51.2 ± 3.2 | - « - | 50.7 ± 3.2 |
| 9 | - « - | 49.4 ± 3.2 | - « - | 51.2 ± 1.7 |
| 10 | - « - | 48.4 ± 2.4 | - « - | 49.8 ± 2.0 |
| 15 | - « - | 47.3 ± 1.8* | - « - | 49.3 ± 1.4 |
| 21 | - « - | 49.6 ± 1.7 | - « - | 49.7 ± 2.1 |
| 25 | - « - | 50.3 ± 2.1 | - « - | 50.1 ± 3.0 |
| 28 | - « - | 50.9 d 2.7 | - « - | 50.4 ± 3.0 |
| 31 | - « - | 47.5 ± 1.7* | - « - | 49.5 ± 1.2 |
| 36 | - « - | 49.3 ± 2.6 | - « - | 49.7 ± 1.8 |
| 37 | - « - | 48.1 ± 2.9 | - « - | 50.1 ± 1.0 |

Note:
*valid at $p \leq 0.05$

From the data given in Table 3 it is evident that on the ADP model of the induced aggregations of thrombocytes the administration of the compounds according to the invention at a concentration of $10^{-3}$ M initiates a drop of the plasma optical density in a range of 5.4% to 36.5% compared to the control. When introducing the compounds at a concentration of $10^{-4}$ M, the effect makes 4.0% to 29.2%. The administration of the compounds according to the invention into plasma enriched with thrombocytes at a concentration of $10^{-5}$ M, results in depression of the aggregative function of the blood platelets and drop of the optical density by 2.3 to 34.1% compared to the control. Thus, in a range of concentrations $10^{-3}$ M, $10^{-4}$ M, $10^{-5}$ M the investigated compounds accordthen the compounds according to the invention. The doses of the compounds were in a range from 15 to 60 mg/kg. These doses were chosen taking into account the most effective concentration from $10^{-3}$ M to $10^{-5}$ M obtained in the experiments in vitro and stipulated by morphological and functional features of the rabbit organism, such as the rate of biotransformation of the drugs, the ratio of the size of the liver to the whole organism, the filtering capacity of the kidneys, etc.

For leveling the different effects of the compounds in different days due the ambient temperature, humidity and other parameters, 2 animals of each series were taken for experiments every day. Under "series" there is understood a group of 6 animals used for studying one of the doses of the compounds.

The blood for obtaining plasma enriched with thrombocytes was taken from marginal vein of the rabbit ear: in the control group—directly before introducing the tested compounds; in investigated groups—15 minutes after introducing these compounds and then after 30, 60, 120 minutes and so on up to the moment when the effect of suppression of aggregation disappeared.

The quantity of thrombocytes was counted before the experiment and at the end thereof in each plasma sample. The results of the experiments are presented in Table 4.

TABLE 4

Effect of the compounds according to the invention on ADP-induced aggregation of thrombocytes of the rabbits (MA - drop of optical density, % to the control)

| MA, %, Control | Compound | Dose, mg/kg | MA, %, After 15 minutes | MA, %, After 30 minutes | MA, %, After 60 minutes | MA, %, After 120 minutes |
|---|---|---|---|---|---|---|
| 50.1 ± 1.7 | 2  | 15.0 | 44.2 ± 2.0* | 42.2 ± 1.6* | 46.9 ± 1.7* | 49.2 ± 2.0 |
| - « -      | 15 |      | 42.8 ± 1.8* | 41.8 ± 1.5* | 45.6 ± 1.5* | 48.3 ± 2.3* |
| - « -      | 21 |      | 43.5 ± 1.7* | 43.3 ± 1.7* | 46.7 ± 1.5* | 49.1 ± 1.7 |
| - « -      | 37 |      | 42.9 ± 1.6* | 41.9 ± 1.6* | 45.9 ± 1.6  | 48.7 ± 2.1 |
| 61.0 ± 1.3 | 2  | 30.0 | 45.3 ± 2.0* | 43.7 ± 1.7* | 40.1 ± 2.2* | 59.7 ± 2.2 |
| - « -      | 15 |      | 43.2 ± 2.2* | 41.8 ± 1.9* | 37.8 ± 1.8* | 58.1 ± 1.7 |
| - « -      | 21 |      | 46.7 ± 1.9* | 45.4 ± 1.8* | 45.0 ± 1.9  | 60.3 ± 2.1 |
| - « -      | 37 |      | 43.5 ± 2.0* | 42.0 ± 1.4* | 41.6 ± 1.4* | 58.4 ± 1.7 |
| 48.6 ± 1.3 | 2  | 60.0 | 45.2 ± 1.2* | 43.6 ± 2.0* | 47.8 ± 1.5  | 48.0 ± 1.2 |
| - « -      | 15 |      | 43.1 ± 1.5* | 41.3 ± 1.5* | 44.7 ± 0.8  | 47.2 ± 1.6 |
| - « -      | 21 |      | 45.1 ± 0.9* | 43.2 ± 2.0* | 47.3 ± 1.6  | 48.3 ± 1.5 |
| - « -      | 37 |      | 43.4 ± 1.8* | 42.4 ± 0.7* | 46.2 ± 2.0  | 47.3 ± 1.7 |

Note:
*valid at at $p \geq 0.05$

From the data given in Table 4 it is evident that compounds 2, 15, 21, 37 according to the invention in a dose of 30 mg/kg within 15 minutes after the administration suppressed the aggregation of thrombocytes: a decrease of the value of drop of the optical density MA made 17.5% to 34/9% compared to the control. This effect was maintained at the achieved level 15 minutes longer, and then intensified to the 60th minute from the beginning of the experiment. The recovery of the initial value MA was recorded to the end of the observation upon expiration of 120 minutes.

During an increase of the dose to 60 mg/kg a similar picture was observed, though the ability of thrombocytes to patching (MA) was reduced to a range of 1.7% to 17.5% compared to the control. The effect of decrease of the aggregation after 30 minutes of experiment was maintained in a range of 3.5 to 20.1% and disappeared to the 120th minute of observation.

The dose of 15 mg/kg decreased the action of the aggregation inductor in a range of 6.8 to 23% within the first 30 minutes of the experiment. The effect of decrease of the aggregation disappeared to the 120th minute of the experiment.

Conclusions

The results of the conducted investigations have confirmed the fact that the compounds according to the invention at intravenous administration in doses of 15, 30, 60 mg/kg have evident antiaggregative effect whose duration is about 2 hours.

3.2. Interaction of the Compounds According to the Invention with Adenosine-Sensitive Receptors of Erythrocytes.

The interaction of compounds 2, 15, 21, 37 according to the invention with adenosine-sensitive receptors of erythrocytes of female mice of line BALB/c of an age of 8-12 months was investigated.

The dependence of the chemiluminescence intensity of the compounds according to the invention in an alkaline solution of 0.1N NaOH was determined in the presence of hydrogen peroxide being an initiator of chemiluminescence. The chemiluminescence was studied using the «LKB» chemiluminometer.

The erythrocytes of peripheral blood of the mice at first were washed three times by a normal physiological solution with centrifuging and then diluted in the Henks solution without glucose by 10 volumes of distilled water immediately used in the experiment.

At the first stage of the experiments the washed erythrocytes were incubated at a temperature of 37° C. or at 4° C. with solutions of the compounds according to the invention at a concentration of $10^{-7}$ to $10^{-5}$ M for 5-30 minutes, then washed by a normal physiological solution with repeated centrifuging in the cold. The obtained suspension of erythrocytes with the bound compounds according to the invention was placed in 0.1N solution of NaOH with addition of hydrogen peroxide at a final concentration of $10^{-7}$ M. The chemiluminescence intensity was measured. A suspension of erythrocytes without compounds according to the invention was used as a control medium.

Figure 6:
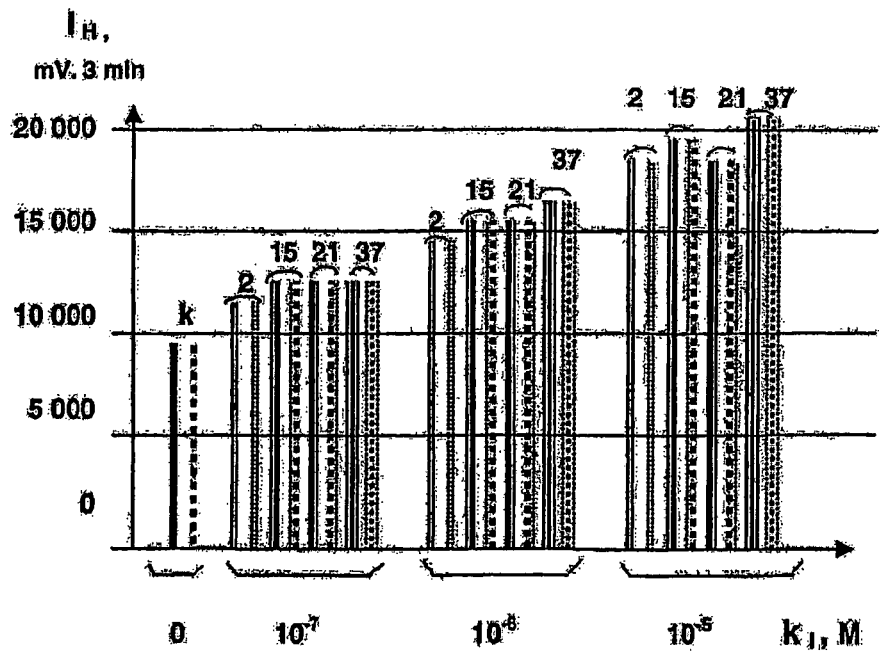
FIG. 6—the intensity of chemiluminescence $I_H$ of a suspension of erythrocytes after incubation with the compounds according to the invention at 37° C. and at 4° C.

The results of the experiments are presented on the chart in FIG. 6, where the values of chemiluminescence intensity $I_H$ in the suspension of erythrocytes are given: in the control medium (line «k») at an incubation temperature of 37° C. (continuous lines on the chart) and 4° C. (dotted lines on the chart) and the same in the experiments after incubation with the investigated compounds (from left to right for compounds 2, 15, 21, 37), at 37° C. (continuous lines) and at 4° C. (dotted lines) at a concentration of $K_i$ from $10^{-7}$ M, $10^{-6}$ M and $10^{-5}$ M. The results have shown that the bond of the compounds according to the invention with the erythrocytes of peripheral blood of the mice does not depend on the temperature, and this, according to the published data, meets the conditions of receptor bonding.

Figure 7A:
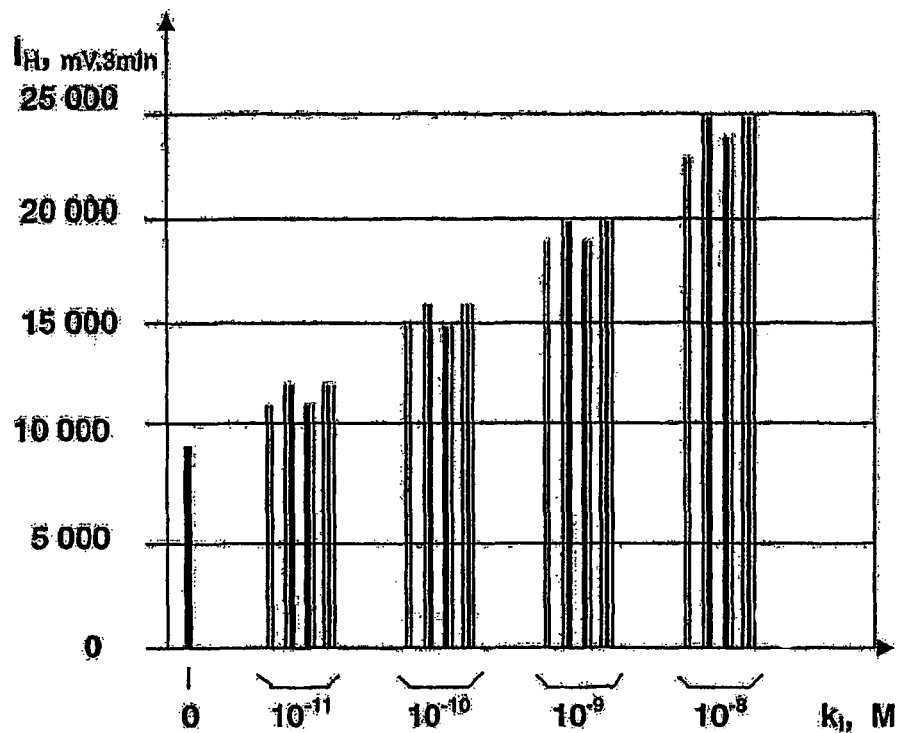
FIG. 7a—the intensity of chemiluminescence $I_H$ of a suspension of erythrocytes after incubation with the compounds according to the invention in concentrations of $10^{-11}$ to $10^{-8}$ M.
Figure 7B:
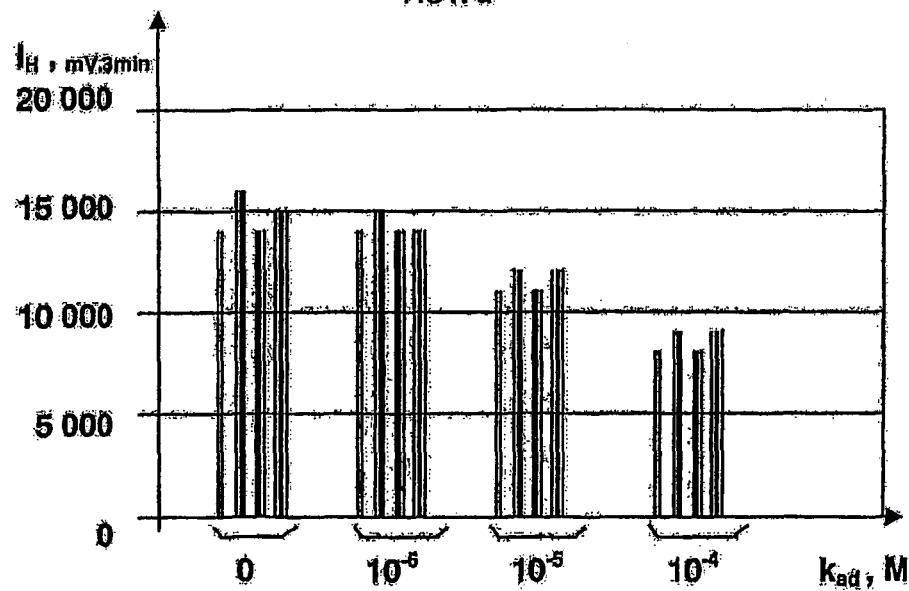
FIG. 7b—the intensity of chemiluminescence $I_H$ of a suspension of erythrocytes after incubation with the compounds according to the invention and an addition of adenosine.

At the second stage of the experiments the washed erythrocytes were incubated at a temperature of 37° C. with solutions of the compounds according to the invention at a concentration of $10^{-11}$ to $10^{-8}$ M during 5-30 minutes, then washed twice with a normal physiological solution by centrifuging in the cold, the obtained suspension was mixed with an adenosine solution at a concentration of $10^{-6}$ to $10^{-4}$ and incubated for 15 minutes, then washed twice with a normal physiological solution with centrifuging in the cold. The obtained suspension of erythrocytes with the compounds according to the invention was placed in 0.1N solution of NaOH with addition of hydrogen peroxide in the final concentration of $10^{-7}$ M. The chemiluminescence intensity was measured. The results of the experiments are presented in FIGS. 7a and 7b.

The chart 7a illustrates the value of chemiluminescence intensity $I_H$ during 3 minutes in the control solution (field 0) and after incubation of the erythrocytes with compounds 2, 15, 21, 37 according to the invention (on the chart in the fields from left to right, respectively) at 37° C. at a concentration of the compounds from $10^{-11}$ M to $10^{-8}$ M.

The chart 7b illustrates the chemiluminescence intensity $I_H$ during 3 minutes after incubation of erythrocytes with compounds 2, 15, 21, 37 (from left to right in the fields) at a temperature of 37° C. (field 0) and with addition of adenosine at a concentration of $10^{-6}$ M, $10^{-5}$ M and $10^{-4}$ M.

As it is evident from the obtained data, the adenosine at a concentration of $10^{-6}$ to 10 M decreases the bonds of the compounds according to the invention with erythrocytes by a factor of 1.5 that can be a result of competitive bonding with receptors of the same type.

Conclusions

Thus, it has been shown that the compounds according to the invention manifest isotropy to adenosine receptors being on both thrombocytes and erythrocytes.

3.3. Interaction of the Compounds According to the Invention with Nuclei-Containing Cells.

The features of interaction of the compounds according to the invention with nuclei-containing cells on an example of spleen cells of mice line BALB/c at the age of 8-12 months were investigated.

The spleen cells were cleaned and washed by centrifuging and suspended in the Henks solution. Then the spleen cells were incubated with compounds 6, 15, 25, 37 at a final concentration of $10^{-5}$ M for 30 minutes at a temperature of 37° C. or 4° C., then washed twice by centrifuging in the cold. After that the chemiluminescence study was effected on the <<LKB>> luminescence meter as described above.

Figure 8:
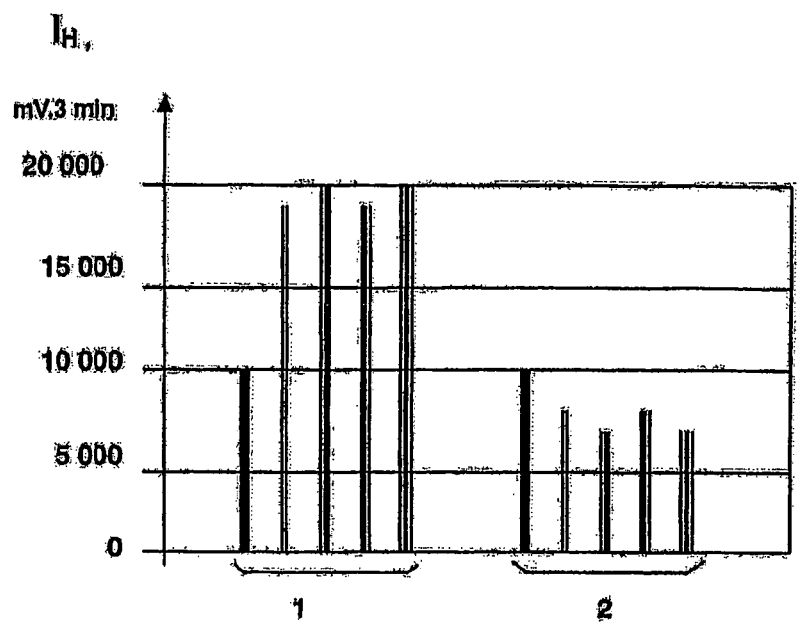
FIG. 8—the intensity of chemiluminescence $I_H$ of the spleen cells after incubation with the compounds according to the invention at 37° C. and at 4° C.

The obtained results are illustrated by the chart in FIG. 8, where in the field 1 there is shown the chemiluminescence intensity $I_H$ of the spleen cells incubated at a temperature of 37° C. without test compounds (control, the first value to the left) and spleen cells incubated with compounds according to the invention (from left to right starting from the second value, respectively, for compounds 6, 15, 25 and 37), and in the field of 2 the chemiluminescence intensity is shown for similar groups of cells and in the same order, incubated at 4° C.

From the chart of FIG. 8 one may make a conclusion that in the nuclei-containing spleen cells, to which the compounds according to the invention are added at a temperature of 37° C., the luminescence level is much higher, than at 4° C. that is evidence of infiltration of these compounds through cellular membrane into the cell cytosol and their bonding with adenosine-sensitive receptors being inside the cell.

Conclusion

The results of the investigations allow us to make a conclusion that the compounds according to the invention are biological isosteres of derivatives of a purine system, in particular, adenosine. The compounds according to the invention are capable of attaching the β-D-ribofuranosic fragment and have a chemical structure similar to adenosine. The compounds can interact with adenine-sensitive receptors lying on the membranes of non-nuclear cells, and can penetrate through the membranes of nuclei-containing cells. These properties of the compounds according to the invention give rise to a possibility of effecting adenosine-dependent enzymes performing the functions, for example, inherent in nicotinamide coenzymes such as nicotineamidedeninnucleotide $NAD^+$ and its phosphorylated derivative $NADPh^+$ or flavin-dependent coenzymes $FAD^+$ being important biological carriers of hydrogen atoms.

4. Effect of the Compounds According to the Invention on Hemostasis.

It is well known that the normally functioning hemostasis system must preserve the liquid state of blood within the vessels that is provided by the powerful anticoagulative blood system and fast thrombosing of the injured sections to prevent hemorrhage and intramuscular hemorrhage. This is aided by some factors of blood plasma, thrombocytes and tissues.

It is assumed that a living organism has specific inhibitors for each factor of blood coagulation. A decrease of the activity of these inhibitors increases the blood coagulation and promotes formation of thrombuses. An increase of the activity of these inhibitors hampers the blood coagulation and can be accompanied by development of hemorrhage.

The compounds according to the invention were tested for their effect on the blood plasma factors, in particular, on the plasma hemostasis condition.

The investigations were performed on 72 rabbits of the "Chinchilla" breed with a mass of 2.5±0.3 kg, who were administered which solutions of compounds 2, 15, 21, 37 in doses of 15, 30 and 60 mg/kg intravenously. The experiments included the thrombin-test (series No. 7300) and the coagulability-test (series No. 5000) purchased from the scientific-and-production association (SPA) "Renam", thromboplastin (series No. 240600) and calcium chloride purchased from the SPA "MedioLab"

The static parameters of the blood and plasma coagulation (partial activated thromboplastin time, thrombin time, maximum coagulation activity (test for auto coagulation) were determined using the Behnk Electronic coagulometer (Germany). The operating principle of this instrument is based on the fact that the formed blood clot breaks the contacts of the pulse counter in the flask-pin circuit, said pin permanently oscillating in a vertical plane. The moment of formation of the clot is registered by stopping the stop watch hand.

The measurements were effected at a constant temperature of 37° C. maintained by a temperature control unit.

4.1. The Effect on Partial Activated Thromboplastin Time (PATT).

The PATT is a standard coagulation sample sensitive to deficiency of all plasma factors (except for VII) specifying the condition of the initial stage of the internal coagulation mechanism and indicating to the presence in the blood of substances having anticoagulation properties, for example, those of heparin.

Compounds 2, 15, 21, 37 according to the invention at a concentration of 15, 30 and 60 mg/kg were introduced to the above experimental animals intravenously, and their blood samples were taken off 15, 30, 60 and 120 minutes after the administration.

The blood plasma samples deprived of thrombocytes obtained as described above in an amount of 0.1 ml were put in a coagulometer flask and heated for 1 minute at 37° C., then 0.1 ml of 0.277% solution of calcium chloride was added and the blood clotting time was registered. The coagulation time T in seconds of the control plasma and plasma obtained after intravenous administration after 15, 30, 60 and 120 minutes were compared. The results of the measurements are given in Table 5.

TABLE 5

Effect of the compounds according to the invention on the indexes of PATT of rabbits for intravenous administration

| T, s Control | Compound | Dose, mg/kg | T, s after 15 minutes. | T, s after 30 minutes | T, s after 60 minutes. | T, s after 120 minutes |
|---|---|---|---|---|---|---|
| 37.0 ± 0.2 | 2  | 15.0   | 37.0 ± 0.1 | 37.0 ± 0.2 | 36.9 ± 0.1 | 37.0 ± 0.3 |
| - « -      | 15 | - « -  | 37.0 ± 0.1 | 37.0 ± 0.2 | 36.9 ± 0.1 | 37.0 ± 0.3 |
| - « -      | 21 | - « -  | 37.1 ± 0.1 | 37.2 ± 0.1 | 36.9 ± 0.1 | 37.0 ± 0.2 |
| - « -      | 37 | - « -  | 37.0 ± 0.2 | 37.1 ± 0.1 | 37.0 ± 0.2 | 36.9 ± 0.1 |
| 33.3 ± 0.8 | 2  | 30.0   | 32.7 ± 0.5 | 32.0 ± 0.1 | 32.2 ± 0.1 | 32.1 ± 0.2 |
| - « -      | 15 | - « -  | 32.9 ± 0.8 | 32.1 ± 0.1 | 32.0 ± 0.2 | 32.0 ± 0.1 |
| - « -      | 21 | - « -  | 32.8 ± 0.4 | 32.0 ± 0.1 | 32.2 ± 0.1 | 32.1 ± 0.1 |
| - « -      | 37 | - « -  | 33.1 ± 0.1 | 33.3 ± 0.1 | 33.3 ± 0.2 | 33.0 ± 0.4 |
| 32.5 ± 0.3 | 2  | 60.0   | 32.3 ± 0.2 | 32.4 ± 0.1 | 32.3 ± 0.1 | 32.4 ± 0.1 |
| - « -      | 15 | - « -  | 32.2 ± 0.1 | 32.2 ± 0.1 | 32.1 ± 0.2 | 32.2 ± 0.1 |
| - « -      | 21 | - « -  | 32.0 ± 0.4 | 32.1 ± 0.2 | 32.0 ± 0.1 | 32.3 ± 0.2 |
| - « -      | 37 | - « -  | 32.5 ± 0.1 | 32.3 ± 0.2 | 32.4 ± 0.1 | 32.6 ± 0.3 |

From the data of Table 5 it is clear that the experimental compounds 2, 15, 21, 37 according to the invention in doses 15.0, 30.0, 60.0 mg/kg do not affect the PATT.

4.2. The Effect on Prothrombin Time.

The "prothrombin time" is an important indicator of the hemostasis condition, which is widely used in experimental and clinical medicine.

The method of its determination is based on estimation of the coagulation of citrate or oxalic blood plasma, when it is mixed with thromboplastin and a calcium chloride solution. Since under these conditions the time of formation of the clot depends on the content of II, VII, IX and X factors in the investigated plasma sample, now the test is called "thromboplastin time by Quick" or "activity thromboplastin complex".

Compounds 2, 15, 21, 37 according to the invention at a concentration of 15, 30 and 60 mg/kg were administered to the above experimental animals intravenously and their blood was taken off after 15, 30, 60 and 120 minutes after the administration.

Citrate blood containing 1 part of citrate per 9 parts of native blood was centrifuged at 3000 rev/min for 10 minutes to obtain plasma deprived of thrombocytes.

Added into a test tube in a water bath were 0.1 ml of plasma and 0.1 ml of a thromboplastin solution. After 60 seconds, 0.1 ml of 0.277% solution of calcium chloride was added and the time of reaction $T_1$ in seconds was registered. The results of the tests are given in Table 6.

From the data given in Table 6 it is evident that investigated compounds 2, 15, 21, 37 according to the invention taken in doses of 15.0, 30.0, 60.0 mg/kg have no effect on the prothrombin time index.

4.3. The Effect of Autocoagulation Test on Blood

This parameter characterizes the dynamics of increase and subsequent inactivation of the thromboplastin-thrombin activity of the blood being investigated.

Compounds 2, 15, 21, 37 according to the invention at a concentration of 15, 30 and 60 mg/kg were intravenously administered to the above experimental animals and their blood samples were taken off 15, 30, 60 and 120 minutes after the administration.

Added to 0.2 ml of plasma obtained by centrifuging citrate blood at 1500 rev/min within 10 minutes was a glycosylate-calcium mixture (2.0 ml 0.222% $CaCl_2$+0.1 ml of investigated citrate blood) 4, 6, 8, 10 minutes after the preparation of this mixture and the time of coagulation in the sample was determined.

The obtained results in seconds were translated in factors of coagulating activity A in percent, which specify the state of both the coagulating and anticoagulating parts of the blood coagulating system. The results of the experiments are given in Table 7.

The effect of the compounds according to the invention on the values of coagulating activity A by the data of autocoagulation test with intravenous administration of the compounds to the rabbits

TABLE 6

The effect of the compounds according to the invention on the prothrombin time of rabbits with intravenous administration of the compounds

| T, s Control | Compound | Dose, mg/kg | T, s after 15 minutes. | T, s after 30 minutes. | T, s after 60 minutes. | T, s After 120 minutes |
|---|---|---|---|---|---|---|
| 11.8 ± 0.1 | 2  | 15.0  | 11.7 ± 0.2 | 11.5 ± 0.2 | 11.4 ± 0.2 | 11.7 ± 0.1 |
| - « -      | 15 | - « - | 11.5 ± 0.2 | 11.7 ± 0.2 | 11.2 ± 0.2 | 11.5 ± 0.2 |
| - « -      | 21 | - « - | 11.4 ± 0.2 | 11.5 ± 0.1 | 11.3 ± 0.1 | 11.5 ± 0.2 |
| - « -      | 37 | - « - | 11.6 ± 0.2 | 11.6 ± 0.1 | 11.5 ± 0.2 | 11.8 ± 0.1 |
| 11.2 ± 0.1 | 2  | 30.0  | 11.1 ± 0.2 | 11.0 ± 0.1 | 11.3 ± 0.1 | 11.2 ± 0.2 |
| - « -      | 15 | - « - | 11.0 ± 0.2 | 11.2 ± 0.2 | 11.4 ± 0.2 | 11.3 ± 0.2 |
| - « -      | 21 | - « - | 11.2 ± 0.1 | 11.2 ± 0.1 | 11.3 ± 0.2 | 11.2 ± 0.2 |
| - « -      | 37 | - « - | 11.3 ± 0.1 | 11.2 ± 0.2 | 11.4 ± 0.1 | 11.1 ± 0.1 |
| 12.0 ± 0.1 | 2  | 60.0  | 12.0 ± 0.1 | 11.9 ± 0.2 | 12.1 ± 0.2 | 11.9 ± 0.1 |
| - « -      | 15 | - « - | 12.0 ± 0.1 | 12.0 ± 0.1 | 12.0 ± 0.2 | 12.0 ± 0.1 |
| - « -      | 21 | - « - | 12.0 ± 0.2 | 11.8 ± 0.1 | 12.1 ± 0.1 | 12.0 ± 0.2 |
| - « -      | 37 | - « - | 12.1 ± 0.1 | 12.0 ± 0.1 | 12.1 ± 0.2 | 12.0 ± 0.1 |

TABLE 7

| A, % Control | Compound | Dose, mg/kg | A, % after 15 minutes | A, % after 30 minutes | A, % after 60 minutes | A, % after 120 minutes. |
|---|---|---|---|---|---|---|
| 85.6 | 2 | 15.0 | 80.2 | 100.0 | 87.4 | 98.0 |
| -«- | 15 | , | 82.3 | 103.0 | 89.0 | 101.2 |
| -«- | 21 | -«- | 81.4 | 101.3 | 86.5 | 97.4 |
| -«- | 37 | -«- | 82.1 | 102.8 | 88.7 | 100.6 |
| 70.0 | 2 | 30.0 | 98.4 | 71.2 | 104.2 | 70.9 |
| -«- | 15 | -«- | 100.3 | 68.4 | 106.6 | 70.6 |
| -«- | 21 | -«- | 97.2 | 69.1 | 103.7 | 71.0 |
| -«- | 37 | -«- | 99.8 | 68.3 | 105.8 | 70.4 |
| 65.9 | 2 | 60.0 | 72.3 | 60.8 | 62.5 | 65.7 |
| -«- | 15 | -«- | 74.4 | 63.2 | 64.4 | 66.5 |
| -«- | 21 | -«- | 71.9 | 62.1 | 63.7 | 66.2 |
| -«- | 37 | -«- | 74.3 | 63.0 | 64.2 | 66.3 |

From the data given in Table 7 it is evident that the investigated compounds 2, 15, 21, 37 according to the invention in doses 15.0, 30.0, 60.0 mg/kg have no effect on the coagulation activity according to the data of the autocoagulation test.

4.4. Effect on the Thrombin Time

The "thrombin time" characterizes the rate of transformation of fibrinogen into fibrin. It was determined by measuring the coagulation time of plasma deprived of thrombocytes under the effect of thrombin standardized by the control plasma.

0.2 ml of a thrombin solution was added to 0.2 ml of the test blood plasma of experimental animals, from whom the blood was taken 15, 30, 60 and 120 minutes after the intravenous administration of compounds 2, 15, 21, 37 according to the invention in doses of 15, 30, 60 mg/kg incubated for 1 minute at a temperature of 37° C. and the time of formation of clot $T_2$ in seconds in a coagulometer of the Behnk Electronic Company (Germany). The test results are given in Table 8.

TABLE 8

The effect of the compounds according to the invention on the thrombin time of plasma of rabbits subjected to intravenous administration of the compounds

| $T_2$, s Control | Compound | Dose, mg/kg | $T_2$, s after 15 minutes | $T_2$, s after 30 minutes | $T_2$, s after 60 minutes | $T_2$, s After 120 minutes |
|---|---|---|---|---|---|---|
| 15.8 | 2 | 15.0 | 16.2* | 17.0* | 16.0* | 15.3* |
| -«- | 15 | -«- | 17.0* | 18.5* | 16.5* | 15.5* |
| -«- | 21 | -«- | 16.4* | 17.7* | 16.1* | 15.7* |
| -«- | 37 | -«- | 16.9* | 18.2* | 16.3* | 15.6* |
| 14.7 | 2 | 30.0 | 17.8* | 18.4* | 19.2* | 15.3* |
| -«- | 15 | -«- | 19.7* | 20.5* | 21.3* | 15.0* |
| -«- | 21 | -«- | 17.9* | 18.8* | 19.0* | 15.6* |
| -«- | 37 | -«- | 19.5* | 20.3* | 21.0* | 15.2* |
| 15.2 | 2 | 60.0 | 16.0* | 16.9* | 15.9* | 15.3* |
|  | 15 | -«- | 16.8* | 18.0* | 16.5* | 14.7* |
|  | 21 | -«- | 16.2* | 17.7* | 16.3* | 15.7* |
|  | 37 | -«- | 16.6* | 17.8* | 16.2* | 15.0* |

Note:
*stands for a reliable value compared to the control at $p \leq 0.05$.

From the data, given in Table 8 it is evident that in a of dose 15.0 mg/kg the administration of the compounds according to the invention increases the thrombin time to the 15th minute of the observation, this effect reaching its maximum to the 30th minute, weakening during the following half an hour and completely disappearing to the 120th minute. Similar results were obtained with administration of the compounds in a dose of 60.0 mg/kg. The effect of the compounds on this hemostasis index increased only at a dose of 30.0 mg/kg: the blood clotting time was gradually enlarged within the first 25 minutes of the experiment, reaching the maximum to the 60th minute, and then was normalized to the 120th minute of the experiment.

Conclusions

The data obtained prove that the compounds according to the invention do not influence the pathological effect on a normally functioning hemostasis system.

5. The Effect of the Compounds According to the Invention on Processes of Production and Bonding of Active Forms of Oxygen.

The study of the effect of the compounds according to the invention on the activity of three most important oxidizing system enzymes of an organism: catalases, peroxidases and superoxydismutases was of great interest. These enzymes are accessible for determining in blood of human and animals and reflect three different levels of inactivation of active forms of oxygen: hydrogen peroxide, superoxidic radicals and intermediate forms of their exchange.

Free oxidation proceeds with participation of free-radical forms of oxygen, which are formed during one-electron reduction of oxygen and, first of all, superoxide-anion of oxygen radical $O_2^-$. This radical can be formed also at a change of conditions of functioning of a respiratory system and under effect of ultraviolet radiation, as well as during the reaction of oxygen with ions of metals of variable valence, mainly with iron $Fe^{2+}$ and can be produced in the cells by enzymes, such, as xanthinexydase or NADPhH oxydase. It is a highly reactive and hydrophilic compound that cannot abandon the cell and is collected in the cell cytosol.

The living cells have systems of protection against high production of free radicals. The enzyme superoxidedismutase SOD transforms superoxide-anion radical of oxygen into less reactive and more hydrophobic hydrogen peroxide $H_2O_3$. Hydrogen peroxide is a substrate for catalase and glutathione-dependent peroxidases which catalyze its transformation into molecules of water. An intensive generation of free radicals accompanies pathological condition, for example, the Parkinson's disease, Alzheimer's disease, and processes of biological aging. However, complete suppression of the peroxide processes in tissues is undesirable, because free radicals have useful properties. They induce apoptosis, participate in the formation of cellular immunity, adjust fatty-acid composition of lipid molecules in the cellular membrane.

It is well known that cyclic hydrazides of aromatic and heterocyclic orthodicarboxylic acids are capable of reacting with active forms of oxygen, in particular, with superoxide-anions, hydroxyl radicals and hydroperoxide radicals $HO_2^-$ that is characterized by the phenomenon of chemiluminescence of said cyclic hydrazides (Brenton P. D. "Mechanistic Aspect of Diazaquinone Chemiluminescence. Aust. J. Chem., 1984, v. 37, p. 1001-1008).

The inventors have studied the capacity of the compounds according to the invention of penetrating through a cellular membrane and binding excessively produced superoxide-anions of oxygen.

5.1. The Effect of the Compounds According to the Invention on the Sod Activity of Bonding Superoxide-Anion Radicals.

The effect of the compounds according to the invention on the bonding of superoxide-anions of oxygen by superoxidismutase SOD was investigated.

The method is based on a competition of SOD or compounds according to the invention with nitroblue tetrazole (TTNB) for superoxide-anions formed during the aerobic reaction of NAD-H and phenosemetasulfate (FMS). It is known that in the presence of SOD the reduction of TTNB decreases. In the case of interaction of the compounds according to the invention with superoxide-anion radicals, the reduction of TTNB will also decrease (Nishikimi M. Rao N. A. and Yagi K. "The occurrence of superoxide anion in the reaction of reduced phenasine methosulfate and molecular oxygen". Biochem. Biophys. Res. Commun, 1972, v. 46, p. 849-855).

The process may be presented by the following scheme:
1) NAD-H+FMS→superoxide-anion radical+$NAD^+$+reduced FMS
2) SOD+superoxide-anion a radical→inactivated superoxide (or a compound according to the invention)
or TTNB+superoxide-anion radical→reduced TTNB.

The intensity of generation and interception of a superoxide-anion radical was recorded at 560 HM by the degree of blocking the reaction of reduction of TTNB by the superoxidedismutase or investigated compounds. In so doing the activity of SOD or investigated compounds according to the invention was estimated taking 50% inhibition of reduced TTNB formation as a unit of activity. Depending on the effect of the compounds according to the invention, the SOD activity was expressed in units per minute on conversion to 1 mg of lysate of erythrocytes.

Erythrocytes of female mice of BALB/c line aged 3 months were washed with centrifuging and lysed with 10 volumes of distilled water. The hemolysate was then incubated for 30 minutes at 37° C. with compounds 3, 15, 23, 37 according to the invention at at different concentrations, mkM: 10.0; 50.0; 100.0. The SOD activity was also measured.

Figure 9:
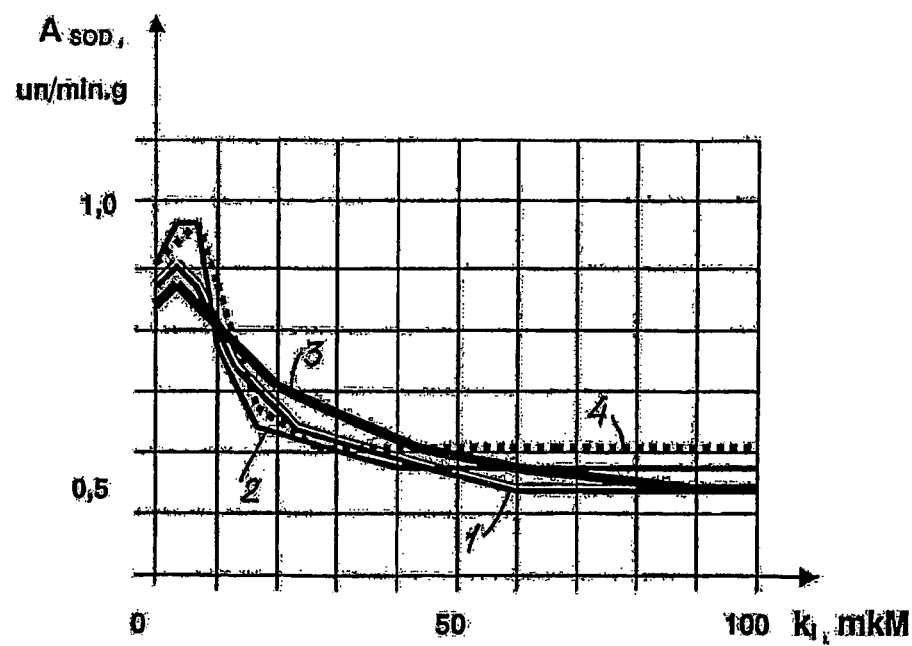
FIG. 9—the effect of the compounds according to the invention on the superoxidedismutase activity.

The results of the experiments are presented on the graphs of FIG. 9, where curves 1, 2, 3, 4 show the SOD activity $A_{SOD}$ after incubation with compounds 3, 15, 23, 37, respectively.

From the graphs of FIG. 9 it is clear that the presence of the compounds according to the invention inhibits the SOD activity depending on the dose that is explained by competitive bonding of the superoxide-anion radicals by the compounds according to the invention.

5.2. The Effect on Production of Superoxide-Anion Radicals.

A possible effect of compounds 3, 15, 23, 37 according to the invention at concentrations of 10, 50, 100 mkM on the formation of superoxide-anion radicals in reaction NAD-H+FMS+TTNB was investigated. This effect was estimated by a change of the optical density of the solutions during the formation of reduced TTNB.

HCT at a final concentration of 0.7 mM, FMS—33 mkM, NAD-H—70 mkM and the investigated compounds at different concentrations in the Henks solution were used. The reaction mass was incubated for 10 minutes at a temperature of 37° C. A change of the light-permeable capacity C of the reaction mixture was recorded in a spectrophotometer at 560 HM and was estimated in percent relative to an accepted light-pass standard in the model of reaction NAD-H+FMS+TTNB using, instead of the compounds according to the invention, SOD of erythrocytes 98% purity (recombinant human SOD). The test results are given on the graphs of FIG. 10, where curves 1, 2, 3, 4 illustrate the effect of the compounds 3, 15, 23, 37, respectively, on the SOD activity.

Figure 10:
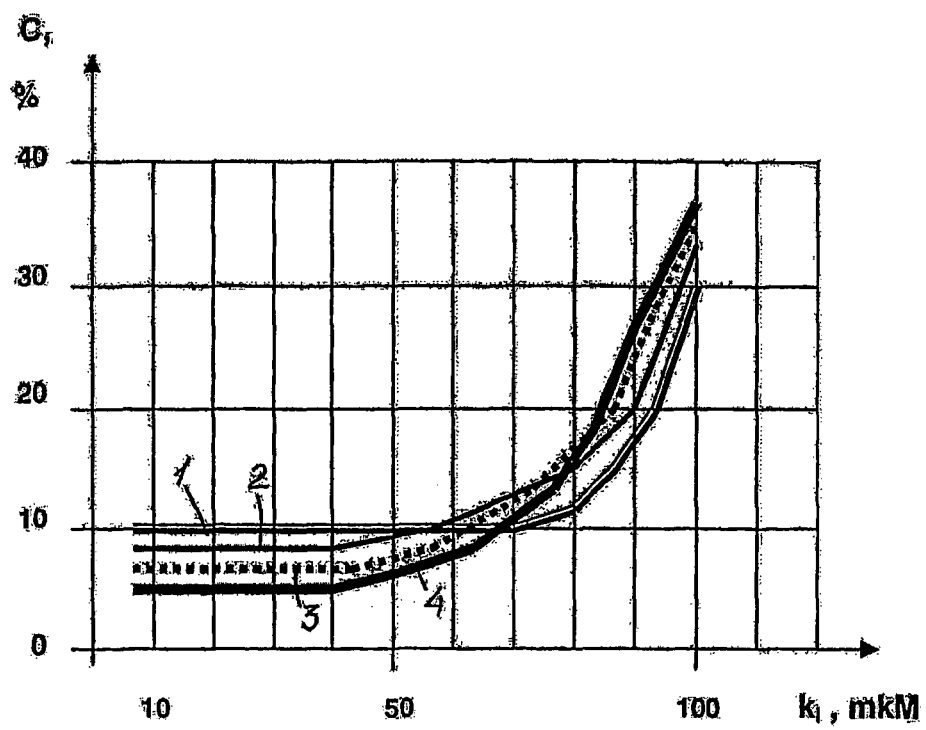
FIG. 10—the effect of the compounds according to the invention on the formation of superoxide-anion radicals in the cells.

From the graphs in FIG. 10 it is evident that the investigated compounds can bind the formed superoxide-anion radicals depending on a dose used.

5.3. The Effect of the Compounds According to the Invention on the Catalase and Peroxidase Activity.

The methods of determining the catalase activity is based on quantitative determination of the rate of decomposition of hydrogen peroxide, which is a specific substrate for this enzyme. The processes of competitive interaction of compounds 3, 15, 23, 36 according to the invention with hydrogen peroxide were investigated.

To determine the catalase activity, the inventors used the method of spectrophotometric analysis of the products formed during the reaction of hydrogen peroxide with ammonium molybdate. This reaction is quick running and results in formation of stable products.

2.0 ml of 0.03% hydrogen peroxide (standard) were added to 0.1 ml of homologinated erythrocytes of blood of mice, line BALB/c, or such a mixture was prepared with addition of one of compounds 3, 15, 23, 36 according to the invention at concentration of 1.0 or 10.0 mkg/ml (experiment) and then in different experiments 1.0 ml of 4% solution of a ammonium molybdate was added over 10, 20, 30, 60, 90, 120 minutes. The reaction is accompanied by fast and irreversible decomposition of the hydrogen peroxide with formation of colored products. The light absorption of the obtained solutions was measured at 410 nm, the test flask was 1 cm thick, distilled water being used in a control flask.

Figure 11:
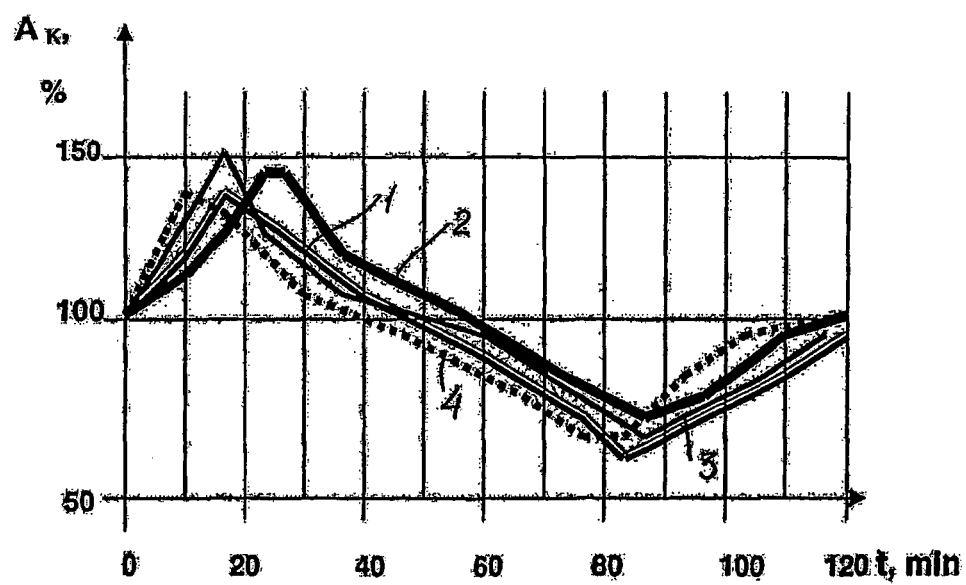
FIG. 11—the effect of the compounds according to the invention on the catalase activity.

The results of the investigations are presented on the graphs of FIG. 11, the catalase activity being expressed in relative values $A_K$. Curves 1, 2, 3, 4 illustrate the effect of compounds 3, 15, 23, 36, respectively, at a concentration of 1.0 mkg/ml on the catalase activity during time t of the experiment. The same dependence was observed for a concentration of 10.0 mkg/ml (not shown on the graph).

The measurement of the peroxidase activity is of considerable interest in clinical practice. For this purpose, use is made of a method based on oxidation of indigo carmine in ascent medium.

Added to 2.0 ml of and acetate buffer solution was 0.1 ml of homologinated erythrocytes of blood of mice, line BALB/c, then 2.0 ml of 0.03% hydrogen peroxide (control) solution was added to the mixture or the same mixture was prepared with addition of compounds 3, 15, 23, 36 according to the invention at a concentration of 1.0 or 10.0 mkg/ml (experiment). After that in different experiments 1.0 ml of indigo carmine was added to the mixture over 10, 20, 30, 60, 90, 120 minutes. The time of reaction with indigo carmine was recorded in seconds by a change of the solution color from dark blue through green in colorless and then in pink. In the experiments the time of the end of the reaction was fixed when the color transformed into colorless.

Figure 12:
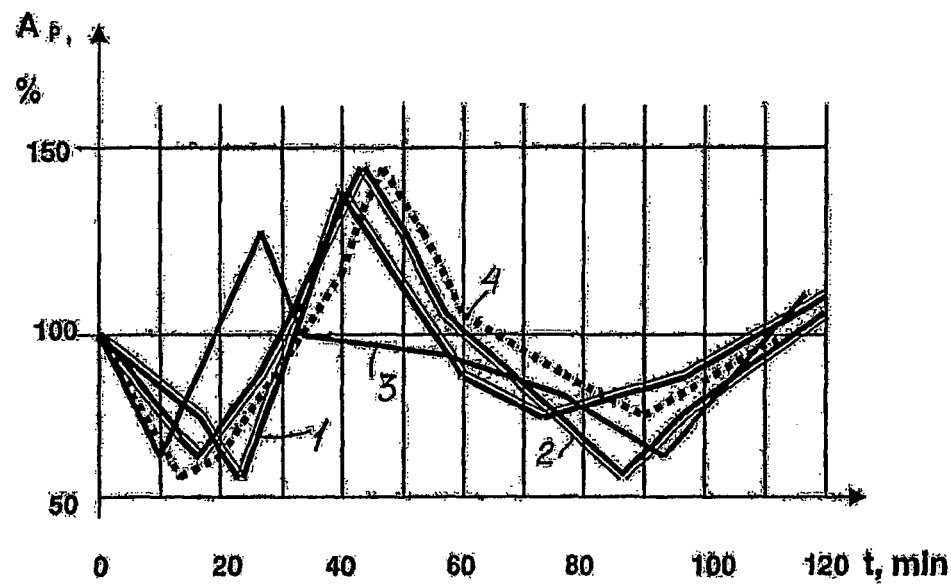
FIG. 12—the effect of the compounds according to the invention on the activity of the peroxidase of erythrocytes.

The obtained results are presented in relative values $A_p$ on the graphs in FIG. 12 by curves 1, 2, 3, 4 for compounds 3, 15, 23, 36 according to the invention at a concentration of 1.0 mkg/ml, a similar dependence being observed for a concentration of 10.0 mkg/ml (not shown on the graphs).

Conclusions

Thus, the compounds according to the invention have a pronounced effect on the activity of the most important enzymes of the oxidizing system of an organism, i.e. catalase, peroxidase and superdismutase. In so doing the effect on the kinetics of the enzymes is of an oscillatory character with a limited amplitude, and this points to a regulatory action on the compounds according to the invention and transfer of the enzymes to a regime of active adaptation to the new conditions. Besides, it has been found that the compounds according to the invention are capable of reacting with excessive oxygen produced in the cell.

6. The Effect of the Compounds According to the Invention on Development of Oxidizing Stress.

It is well known that under the oxidizing stress conditions raised due to excessive formation of active forms of oxygen or highly reactive nitrogen metabolites, many biochemical characteristics of blood in the cell change and nitrergic mechanisms of the cells are distorted.

The model of morphine abstinence in rats, which is an analogue of heroin abstinence of a human being was taken as a model of creation of an oxidizing stress in cells.

The physical dependence on morphine was simulated on male rats Wistar with a mass of 250-350 grams and aged 6 months by intraperitoneal administration of morphine with hydrochloride within 6 days, 2 times a day (at $10^{00}$ and $20^{00}$) in increasing doses according to the scheme, mg/kg: 10.10; 20.20; 40.40; 60.60; 80.80; 100.100 (Rahman S., Ali Khan R., Kumar A. "Experimental study of the morphine deaddiction properties of Delphinium denudatum Wall//BMC Complement Altern". Med. 2002, v. 29, p. 1-6; Dum J., Blasig J., Herz A. Buprenorphine: "Demonstration of physical dependence liability". Eur. J. Pharmacol., 1981, v. 70. p. 293-300).

The experiments were carried out on rats in series of 7 animals on each compound according to the invention. Non-morphinized animal with not administered with compounds according to the invention were used as a control group. The first experimental group consisted of animals morphinized by the above-described technique, the second group consisted of animals treated with compounds 6, 15, 25, 37 according to the invention by intramuscular injection in a dose of 20.0 mg/kg three times a day, the third group consisted of morphinized animals, which three times a day following the last dose of morphine injection, were administered with compounds 6, 15, 25, 37 according to the invention intramuscularly in a dose of 20.0 mg/kg. Then the rats were decapitated, the blood from somnolent arteries was collected in test tubes with solution EDTA as an anticoagulant, centrifuged at 1500 g for 15 minutes at 4° C.

6.1. The Effect of the Compounds According to the Invention on the Activity of Enzymes in Blood Plasma To estimate possible hepatoprotective action of the compounds according to the invention under conditions of development of an oxidizing stress in the liver cells, effect of these compounds on the most important biochemical blood indexes, in particular, on the content in blood plasma of indicator enzyme of aspartateaminotransferase (AST), alanineaminotransferase (ALT), γ-glutamiletranspeptidase (γ-GTP) was investigated. The content of enzymes was estimated by their catalyzing activity in blood plasma.

It is well known that morphine abstinence results in increased activity of enzymes AST and γ-GTP in blood plasma that indicates to toxic action of morphine on the liver of the animals.

The activity of AST, ALT and γ-GTP was determined by means of diagnostic sets DiaSys, Germany. The results of the tests are given in Table 9.

TABLE 9

The effect of morphine and compounds according to the invention on the content of $C_i$ of indicator enzymes in blood plasma

| Enzyme | $C_i$, mE/l Control | $C_i$, mE/l control + Morphine | Compound | $C_i$, mE/l Control + compound | $C_i$, mE/l control + Morphine + Compound |
|---|---|---|---|---|---|
| ALT | 106.76 ± 111.35 | 116.12 ± 110.44 | 6 | 114.5 ± 1.13 | 122.44 ± 2.01 |
| | | | 15 | 113.48 ± 2.39 | 121.08 ± 5.04 |
| | | | 25 | 115.27 ± 1.09 | 121.96 ± 3.4 |
| | | | 37 | 113.84 ± 2.0 | 120.84 ± 5.20 |
| AST | 179.881 ± 11.94 | 238.201 ± 14.71 | 6 | 176.18 ± 3.26 | 198.34 ± 9.32 |
| | | | 15 | 173.46 ± 5.63 | 195.57 ± 18.68 |
| | | | 25 | 177.34 ± 6.13 | 196.46 ± 15.34 |
| | | | 37 | 174.82 ± 4.91 | 193.58 ± 14.18 |
| γ-GTP | 6.261 ± 1.80 | 16.80 ± 13.32 | 6 | 8.27 ± 2.12 | 12.52 ± 2.02 |
| | | | 15 | 7.03 ± 2.82 | 10.69 ± 1.84 |
| | | | 25 | 7.57 ± 1.93 | 11.37 ± 1.54 |
| | | | 37 | 8.14 ± 2.64 | 10.32 ± 2.67 |

From the data given in Table 9 it is evident that during the administration of the compounds according to the invention the activity of enzymes AST and γ-GTP did not change and conforms to the indexes of the control group. The administration of morphine resulted in an increase of the activity of said enzymes in blood that indicates to disturbance of the liver activity. The subsequent administration of the compounds according to the invention resulted in normalization of the liver activity and elimination of the consequences of the action of morphine on the cells of the rat liver.

6.2. The Effect of the Compounds According to the Invention on Endocellular Metabolic Processes To estimate the intensity of metabolism of nitrogen oxide in rats, quantitative determination of stable metabolites of nitrogen oxide—nitrites and nitrates $NO_x^-$ in the blood plasma, supernatanates of the liver and thymus gland, a study was conducted by a spectrometric method, and in the brain supernatanates by a photofluorographic method.

The spectrometric method is based the reaction of nitrites with the Griss reagent (a mixture of 2% solution of sulfanilamide and 0.2% N-(1-naphthyl)ethylene diamine. At the first step the nitrite reacts with sulfanilamide with formation of diazonium salt, and then with the second component to form azo dye with an adsorption maximum at 540 nm. For reduction of nitrates into nitrites, a fermentative method was used with bacterial reductase nitrate (Grisham M. B. et al., 1995). The samples of plasma and supernathant of the liver deproteinizated at 100° C. for 5 minutes incubated for 30 minutes at 37° C. in 50.0 mM of HEPES pH 7.4 in the presence of 0.2 unit/ml of *Aspergillus* reductase nitrate, 5.0 mkM of FAD and 0.1 mM of NAD-Ph. At the end of the reaction lactate dehydrogenase and pyruvate were added for isolation of NAD-Ph interfering with the Griss reaction. Then the Griss reagent was added and after 10-minute incubation the light absorption of the samples was measured at 540 nm. To amount of $NO_x^-$ was calculated using sodium nitrate as a standard.

The fluorometric method is based on calculation of the nitrite level by the intensity fluorescence of 2,3-diaminonaphthotriazole, a product of reaction of 2,3-diaminonaphthalene (DAN) and nitrite in an acidic medium (Misko T. R., Schilling R. J., Salvemini D. et al. "A fluorometric assay for the measurement of nitrite of biological samples". Anal. Biochem., 1993, v. 214, p. 11-16). The brain supernatants deproteinizated at 100° C. were placed in a nitrite regenerating system containing 0.125 unit/ml of nitrate reductases, 25 mkM NADPh and 25 mkM FAD prepared in a 20-mM Tris-HCl buffer with pH 7.6 and incubated for 30 minutes at 37° C. The lactate dehydrogenase/pyruvate system was used for oxidation of the NADPh. Then 316 mkM of the DAN solution in 0.62 M of hydrochloric acids were added and the mixture was incubated for 10 minutes in darkness.

280 mM of NaOH were added for stabilization of the fluorescence of the formed 2,3-diaminonaphthotriazole. The fluorescence intensity was measured in the spectrofluorimeter Hitachi F-3000 at a wavelength of excitation of 365 nm and an emission of 405 nm. The concentration of $NO_x^-$ in the brain was calculated by means of a standard solution of sodium nitrate.

The effect of compounds 6, 15, 25, 37 according to the invention on the activity of isoform of synthase of nitrogen oxide (NOC) was also studied, in particular, on the activity of $Ca^{2+}$ (independent) and $Ca^{2+}$ (dependent) isoform NOC in the liver of morphinized rats by the radiometric method on the basis of the rate of accumulation of L-citrulline in an oxidation reaction [$^3$H]-arginine catalyzed by NOC (Bredt and Snyder. "Nitric oxide mediates glutamate-linked enhancement of cGMP levels in the cerebellum". Proc. Natl. Acad. Sci. USA, 1989, v. 86, p. 9030-9033). The formation of L-citrulline in this reaction is equivalent to biosynthesis of nitrogen oxide.

The reaction was initiated by adding supernatant of liver, brain or thymus in a reaction medium containing 2.0 mkKu/ml [$^3$H]L-arginine, 20 mM of HEPES pH 7.4, 0.2 mM of $CaCl_2$, 5.0 mkM of FAD, 5.0 mkM of FMN, 1.0 mM of NADPh, 50.0 mkM of $BH_4$ during the study of supernatants of the brain, while during the analysis of supernatants of the liver for inhibition of arginase and recycling of [$^3$H]L-citrulline in [$^3$H]L-arginine, the medium was mixed with 50.0 mM L-valine and 1.0 mM L-citrulline. After 15-60 minutes of incubation at 37° C., the samples were added with suspension Dowex 50WX8-400 ($Na^+$-form), which sorbs unreacted L-arginine but not L-citrulline. After the sorption, the activity of the samples was determined on the scintillation counter SL-4000 "Intertechnique". The activity of $Ca^{2+}$-dependent and $Ca^{2+}$-independent isoform NOC was determined by a difference of the rates of formation of [$^3$H]L-citrulline in three parallel samples containing 2.0 mM of EDTA as a chelator of $Ca^{2+}$ and as an inhibitor of all forms of NOC—2.0 mM of EDTAM L-NAME, and without inhibitors. The activity of enzyme NOC in the investigated supernatant was counted in pmol of [$^3$H]L-citrulline accumulated per unit of time on 1 mg of protein in the supernatant.

Figure 13:
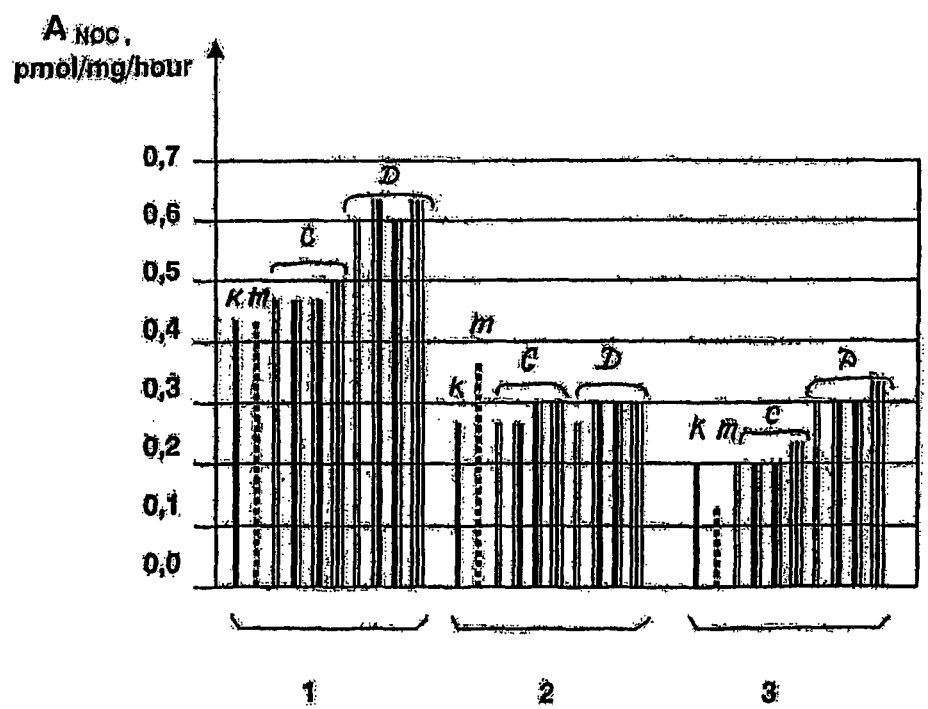
FIG. 13—the effects of the compounds according to the invention on the NOC activity.

The results of the tests are given in Table 10 and in FIG. 13.

TABLE 10

The effect of morphine and compounds according to the invention on the level of nitrites in blood plasma and supernatants of liver and brain and the activity of synthase of nitrogen oxide (NOC) in a brain

| Index | Control | Control + Morphine | Compound | Control + Compound | Control + Morphine + compound |
|---|---|---|---|---|---|
| Nitrites in blood plasma, mkmol/ml | 18.30 ± 2.14 | 12.12 ± 0.61 | 6 | 15.83 ± 1.21 | 15.86 ± 1.20 |
| | | | 15 | 14.39 ± 0.84 | 13.91 ± 1.91 |
| | | | 25 | 17.10 ± 2.05 | 16.78 ± 2.11 |
| | | | 37 | 16.13 ± 1.80 | 15.33 ± 0.87 |
| Nitrites in liver, nmol/mg of protein | 0.260 ± 0.023 | 0.259 ± 0.012 | 6 | 0.245 ± 0.010 | 0.294 ± 0.02 |
| | | | 15 | 0.259 ± 0.019 | 0.285 ± 0.02 |
| | | | 25 | 0.307 ± 0.012 | 0.287 ± 0.01 |
| | | | 37 | 0.262 ± 0.018 | 0.274 ± 0.01 |
| Nitrites in brain, nmol/mg of protein: | | | | | |
| Cortex of cerebrum | 4.63 ± 0.29 | 5.31 ± 0.29 | 6 | 4.59 ± 0.44 | 5.12 ± 0.18 |
| | | | 15 | 4.31 ± 0.37 | 4.72 ± 0.37 |
| | | | 25 | 4.47 ± 0.43 | 4.91 ± 0.32 |
| | | | 37 | 4.36 ± 0.24 | 4.77 ± 0.28 |

TABLE 10-continued

The effect of morphine and compounds according to the invention on the
level of nitrites in blood plasma and supernatants of liver and brain
and the activity of synthase of nitrogen oxide (NOC) in a brain

| Index | Control | Control + Morphine | Compound | Control + Compound | Control + Morphine + compound |
|---|---|---|---|---|---|
| Mesencephalon | 5.66 ± 0.19 | 9.41 ± 1.20 | 6 | 7.01 ± 0.82 | 5.76 ± 0.94 |
| | | | 15 | 6.65 ± 0.70 | 5.50 ± 0.43 |
| | | | 25 | 6.98 ± 1.02 | 5.91 ± 0.74 |
| | | | 37 | 6.84 ± 0.56 | 5.63 ± 0.37 |
| Hypothalamus | 6.57 ± 0.50 | 4.62 d 0.71 | 6 | 6.94 ± 0.67 | 6.72 ± 0.94 |
| | | | 15 | 6.77 ± 0.83 | 6.57 ± 0.88 |
| | | | 25 | 6.87 ± 0.80 | 6.67 ± 0.79 |
| | | | 37 | 6.79 ± 0.92 | 6.52 ± 0.83 |
| Activity of NOC, pmol/min/mg of protein: | | | | | |
| Mesencephalon | 2.18 ± 0.09 | 3.08 ± 0.09 | 6 | 2.84 ± 0.31 | 1.99 ± 0.31 |
| | | | 15 | 2.60 ± 0.29 | 1.83 ± 0.23 |
| | | | 25 | 2.65 ± 0.43 | 1.97 ± 0.27 |
| | | | 37 | 2.62 ± 0.27 | 1.85 ± 0.30 |
| Hypothalamus | 5.37 ± 0.20 | 3.42 ± 0.54 | 6 | 5.93 ± 0.27 | 5.24 ± 0.24 |
| | | | 15 | 5.45 ± 0.24 | 5.26 ± 0.28 |
| | | | 25 | 5.88 ± 0.27 | 5.23 ± 0.27 |
| | | | 37 | 5.61 ± 0.22 | 5.59 ± 0.22 |

From the levels of content of nitrites in blood given in Table 10 it is evident that morphine actually decreased the penetration of nitrites in the blood (at $p \leq 0.02$), and such a decrease of nitrites in blood may be an evidence of a decrease of generation of nitrogen oxide in organs or vessels at morphine abstinence. The compounds according to the invention prevented this effect that can confirm the effect of these compounds on the activity nitrogen oxide synthase in tissues or on the activity of an appropriate enzyme in the vessel endothelia.

In the liver (Table 10) the compounds according to the invention prevented accumulation of peroxidate oxidation products.

In the brain (Table 10) the morphine introduced to the animals has a specific effect on the accumulation of nitrites and the NOC activity: a decrease of nitrergic factors in the hypothalamus and an increase of the same in the cortex of cerebrum and mesencephalon. When only the compounds according to the invention were administered, a decrease of nitrergic factors in the cortex of cerebrum and their increase in a hypothalamus were observed. The subsequent administration of the compounds according to the invention recovered the NOC activity, disturbed by the morphine, in the hypothalamus, mesencephalon, and cortex of cerebrum.

Illustrated on the chart of FIG. 13 is the total NOC activity (field 1 of chart), the activity of the calcium-dependent NOC (field 2) and the activity of the calcium-independent NOC (field 3) in the control (value K), with administration of morphine (value M), with administration of compounds 6, 15, 23, 37 (group C), and administration of the compounds according to the invention after the administration of the morphine (group D), respectively, from left to right in fields 1, 2, 3, 4.

The results of the investigations allow one to make a conclusion that in the liver the activity of isoform NOC reliably changed under the effect of morphine. Compared to the control, the total NOC activity in the morphinized rats and the rats received the compounds according to the invention only did not change. However, the administration of morphine resulted in a rise of activity of the calcium-dependent form NOC and a decrease of activity of the calcium-independent form NOC. The administration of the compounds according to the invention to the morphinized animals resulted in normalization of the activity of the calcium-dependent NOC and in an increase of the activity of the calcium-independent NOC above the initial level that rises total activity of the NOC enzyme.

The effect of the compounds according to the invention on the condition of the thymus of the rats was also investigated: a control group, an experimental group of morphinized animals and an experimental group of animals were first morphinized and then injected with the compounds according to the invention. The experiment was carried out similarly to that described above. The results are given in Table 11.

TABLE 11

The effect of morphine and compounds according
to the invention on the thymus condition

| Index | Control | Administration of morphine | Compound | Administration of compounds | Administration of morphine and compound |
|---|---|---|---|---|---|
| Thymus mass, mg | 230 ± 14 | 145 ± 9 | 6 | 242 ± 17 | 207 ± 14 |
| | | | 15 | 298 ± 25 | 214 ± 12 |
| | | | 25 | 254 ± 14 | 218 ± 17 |
| | | | 37 | 263 ± 21 | 228 ± 15 |

TABLE 11-continued

The effect of morphine and compounds according
to the invention on the thymus condition

| Index | Control | Administration of morphine | Compound | Administration of compounds | Administration of morphine and compound |
|---|---|---|---|---|---|
| Nitrites, nmol/mg of protein Supernatant | 0.331 ± 0.041 | 0.511 ± 0.05 | 6 | 0.424 ± 0.04 | 0.419 ± 0.02 |
| | | | 15 | 0.407 ± 0.02 | 0.383 ± 0.02 |
| | | | 25 | 0.417 ± 0.02 | 0.396 ± 0.02 |
| | | | 37 | 0.410 ± 0.01 | 0.387 ± 0.01 |

From the data given in Table 11 it is evident that the morphine abstinence initiates involution of the thymus, and the compounds according to the invention completely prevent this effect of morphine. Besides, the compounds according to the invention prevent accumulation of nitrites in the thymus.

Conclusions

Thus we may come to a conclusion that the compounds according to the invention feature hepatoprotective action: they prevent rising of activity of the enzymes AST and γ-GTP and stop an oxidizing stress in a liver.

Besides, the compounds according to the invention prevent involution of a thymus, influence different isoforms of synthase of nitrogen oxide, thereby correcting disordered nitrergic mechanisms in a liver, sections of brain and thymus.

7. Estimation of the Total Toxic Action of the Compounds According to the Invention.

The total toxic action of the compounds according to the invention was studied in chronic experiments on rats by introducing preparations in the form of suppositories containing compounds according to the invention as an active ingredient: 5% of active ingredient in the suppository base obtained by molding in a water bath of grades H-15 and W-35 in equal quantities.

The experiments were conducted on inbred rats. The experimental animals were selected in groups by a method of random sampling taking into account the body mass as a determining index; 24 males or 24 females for one preparation from compounds 2, 15, 23, 34, 37 investigated in one dose. 4-5 hours prior to a rectal administration of the preparation, the animals were deprived of feed and the manipulations with animals resulted in a reflex act of a defecation of the rectum cavity.

Two doses of preparations used in the experiments: 50 mg/kg and 500 mg/kg. Before the administration, the suppositories were softened by heating in a glass water bath at a temperature of 38-39° C., the soft mass was collected in tuberculin syringe in a volume of 1 ml, a needle with oliva was attached to the syringe, and the preparatory mass was introduced into the rectum of the animal for a depth of 1.5-2.0 cm. The animals of the control group were administered with sterile medical liquid paraffin in a volume corresponding to the volume of the investigated suppository. A complete course of administration of drugs to the animals was two months. A complex of laboratory diagnostic investigations was carried out one month after the beginning of the administration of the preparation to the animal—in a middle of the course (8 animals), two months after ending the course (8 animals) and three months after ending the recovery period of one month (8 animals). The mass of the body of the rats in the first month of administration of the preparation was determined weekly, and then once in two weeks. On the basis of the dynamics of an index of the mass of the animal body, the volume of preparation being administered was corrected taking into account the test dose. The results of investigations are given in Tables 12, 13 and 14.

TABLE 12

Indexes of peripheral blood of male rats after administration of the investigated drugs
in suppositories in 1 and 2 months

| Blood index | Control 1 month/2 months | Compound | Dose 50 mg/kg 1 month/2 months | Dose 500 mg/kg 1 month/2 months |
|---|---|---|---|---|
| Hemoglobin, Mmol/dm$^3$ | 10.5 ± 0.2/11.4 ± 0.2 | 2 | 10.5 ± 0.1/11.1 ± 0.1 | 10.6 ± 0.1/12.3 ± 0.3* |
| | | 15 | 10.6 ± 0.2/11.2 ± 0.1 | 10.6 ± 0.2/12.5 ± 0.4* |
| | | 23 | 10.7 ± 0.1/11.0 ± 0.1 | 10.7 ± 0.2/12.3 ± 0.3* |
| | | 34 | 10.6 ± 0.1/11.1 ± 0.2 | 10.6 ± 0.3/12.4 ± 0.4* |
| | | 37 | 10.5 ± 0.1/11.0 ± 0.1 | 10.6 ± 0.1/12.1 ± 0.4* |
| Erythrocytes, mln/mm$^3$ | 5.6 ± 0.1/6.1 ± 0.1 | 2 | 5.60 ± 2/6.1 + 0.1 | 5.6 ± 0.1/6.5 ± 0.1* |
| | | 15 | 5.7 ± 0.2/6.0 ± 0.1 | 5.7 ± 0.1/6.7 ± 0.2* |
| | | 23 | 5.7 ± 0.1/6.0 ± 0.2 | 5.7 ± 0.2/6.4 ± 0.2* |
| | | 34 | 5.6 ± 0.1/6.1 ± 0.2 | 5.6 ± 0.2/6.6 ± 0.1* |
| | | 37 | 5.6 ± 0.2/6.2 ± 0.1 | 5.7 ± 0.1/6.5 ± 0.2* |
| Haematocrite, % | 45.9 ± 1.7/45.9 ± 1.8 | 2 | 47.8 ± 1.3/47.9 ± 1.5 | 47.5 ± 1.6/50.3 ± 2.0 |
| | | 15 | 47.9 ± 1.4/47.5 ± 1.2 | 47.6 ± 1.3/53.9 ± 2.1* |
| | | 23 | 47.7 ± 1.2/46.5 ± 1.3 | 47.9 ± 1.1/49.4 ± 1.9* |
| | | 34 | 46.9 ± 1.1/47.5 ± 1.2 | 48.1 ± 1.5/53.1 ± 1.6* |
| | | 37 | 47.8 ± 1.4/47.5 ± 1.2 | 47.9 ± 1.8/52.5 ± 1.7* |
| Average volume of erythrocytes, Mkm$^3$ | 81.4 ± 1.7/74.6 + 1.9 | 2 | 83.4 ± 1.4/77.9 ± 2.1 | 85.2 ± 1.2/72.0 ± 2.5* |
| | | 15 | 84.4 ± 1.5/78.6 ± 1.5 | 82.6 ± 1.1/80.21 ± 1.2* |
| | | 23 | 82.7 ± 1.6/77.5 ± 1.7 | 83.5 ± 1.7/82.1 ± 1.4* |
| | | 34 | 81.6 ± 1.9/76.7 ± 1.9 | 84.1 ± 1.3/83.8 ± 1.5* |
| | | 37 | 83.9 ± 1.7/78.5 ± 1.4 | 82.3 ± 1.5/80.1 ± 1.0* |

TABLE 12-continued

Indexes of peripheral blood of male rats after administration of the investigated drugs in suppositories in 1 and 2 months

| Blood index | Control 1 month/2 months | Compound | Dose 50 mg/kg 1 month/2 months | Dose 500 mg/kg 1 month/2 months |
|---|---|---|---|---|
| Reticulocytes, % | 2.8%0.3/2.9 ± 0.2 | 2 | 2.8 ± 0.2/2.8 ± 0.2 | 2.9 ± 0.3/3.5 ± 0.2 |
| | | 15 | 2.6 ± 0.2/3.0 ± 0.1 | 3.1 ± 0.2/3.3 ± 0.3 |
| | | 23 | 2.7 ± 0.2/2.8 ± 0.1 | 3.1 ± 0.1/3.4 ± 0.1 |
| | | 34 | 2.7 ± 0.1/2.9 ± 0.2 | 3.2 ± 0.2/3.5 ± 0.3 |
| | | 37 | 2.6 ± 0.1/3.1 ± 0.1 | 3.0 ± 0.2/3.4 ± 0.2 |
| Thrombocytes, % | 707 ± 23/593 ± 14 | 2 | 659 ± 26/566 ± 20 | 681 ± 26/583 ± 25 |
| | | 15 | 678 ± 13/597 ± 24 | 683 ± 14/616 ± 40 |
| | | 23 | 659 ± 18/586 ± 28 | 678 ± 18/628 ± 23 |
| | | 34 | 670 ± 23/610 ± 15 | 682 ± 24/631 ± 26 |
| | | 37 | 675 ± 22/609 ± 18 | 671 ± 1 26/639 ± 34 |
| Coagulation, time, seconds | 152 ± 10.2/316 ± 8 | 2 | 145 ± 16/322 ± 18 | 149 ± 11/305 ± 13 |
| | | 15 | 140 ± 12.2/321 ± 12 | 151 ± 6.4/308 ± 16 |
| | | 23 | 150 ± 15/313 ± 17 | 156 ± 11/3171 ± 12 |
| | | 34 | 148 ± 16/321 ± 10 | 165%10/312 ± 9 |
| | | 37 | 151 ± 13/319 ± 12 | 157 ± 14/3161 ± 14 |
| REE, mm/h | 2.2 ± 0.4/1.4 ± 0.2 | 2 | 1.9 ± 0.3/1.7 ± 0.1 | 2.1 ± 0.3/1.9 ± 0.1 |
| | | 15 | 1.8 ± 0.4/1.6 ± 0.2 | 2.2 ± 0.4/1.8 ± 0.4 |
| | | 23 | 1.7 ± 0.8/1.5 ± 0.1 | 2.0 ± 0.3/1.7 ± 0.3 |
| | | 34 | 1.8 ± 0.5/1.7 ± 0.3 | 2.0 ± 0.4/1.8 ± 0.2 |
| | | 37 | 1.8 ± 0.3/1.6 ± 0.3 | 2.2 ± 0.3/2.0 ± 0.1 |
| Leukocyte, thousand/mm$^3$ | 17.4 ± 1.3/19.1 ± 1.9 | 2 | 16.0 ± 1.4/19.3 ± 1.6 | 15.6 ± 0.8/18.6 ± 1.9 |
| | | 15 | 14.8 ± 2.0/16.3 ± 1.0 | 17.0 ± 1.4/21.1 ± 2.4 |
| | | 23 | 15.5 ± 1.1/17.6 ± 1.2 | 16.4 ± 1.1/20.1 ± 1.7 |
| | | 34 | 15.9 ± 1.3/17.8 ± 1.4 | 16.9 ± 1.0/22.1 ± 1.1 |
| | | 37 | 14.9 ± 1.5/16.7 ± 1.2 | 17.1 ± 0.9/18.7 ± 1.7 |
| Basophiles, % | 0 | 2 | 0 | 0 |
| | | 15 | 0 | 0 |
| | | 23 | 0 | 0 |
| | | 34 | 0 | 0 |
| | | 37 | 0 | 0 |
| Eosinophiles, % | 4.0 + 0.3/4.4 + 1.2 | 2 | 3.4 ± 0.6/4.2 ± 0.8 | 3.2 ± 0.9/4.8 ± 1.6 |
| | | 15 | 3.2 ± 1.0/3.6 ± 1.2 | 3.0 ± 1.0/3.2 ± 1.4 |
| | | 23 | 3.6 ± 0.5/4.0 ± 0.7 | 3.3 ± 0.7/3.8 ± 1.3 |
| | | 34 | 3.5 ± 1.0/4.1 ± 0.4 | 3.0 ± 0.9/3.9 ± 1.4 |
| | | 37 | 3.8 ± 0.8/4.2 ± 0.3 | 3.5 ± 1.0/4.1 ± 1.3 |
| Juveniles, % | 0 | 2 | 0 | 0 |
| | | 15 | 0 | 0 |
| | | 23 | 0 | 0 |
| | | 34 | 0 | 0 |
| | | 37 | 0 | 0 |
| Stab neutrophil % | 0.8 ± 0.4/2.4 ± 0.4 | 2 | 0.8 ± 0.3/1.7 ± 0.3 | 0.9 ± 0.2/1.1 ± 0.3 |
| | | 15 | 1.2 ± 0.5/0.8 ± 0.5 | 0.8 ± 0.5/0.8 ± 0.5 |
| | | 23 | 1.1 ± 0.5/1.6 ± 0.2 | 1.0 ± 0.3/1.6 ± 0.2 |
| | | 34 | 1.0 ± 0.4/1.8 ± 0.5 | 0.9 ± 0.2/1.4 ± 0.3 |
| | | 37 | 1.3 ± 0.5/1.9 ± 0.4 | 0.9 ± 0.4/1.1 ± 0.6 |

TABLE 13

The biochemical indexes of blood serum of male rats 1 month after administration of suppositories containing the compounds according to the invention

| Index | Control | Compound | Dose 50 mg/kg | Dose 500 mg/kg |
|---|---|---|---|---|
| Total protein, g/l | 94.89 ± 6.67 | 2 | 87.34 ± 5.56 | 70.84 ± 7.47 |
| | | 15 | 90.22 ± 6.78 | 71.56 ± 8.23 |
| | | 37 | 89.44 ± 7.22 | 70.88 ± 7.24 |
| Glucose, mol/l | 9.76 ± 0.15 | 2 | 9.85 ± 0.37 | 10.20 ± 0.74 |
| | | 15 | 10.00 ± 0.41 | 10.71 ± 0.41 |
| | | 37 | 9.9 ± 0.51 | 10.93 ± 0.84 |
| Urea, Mkmol/l | 8.44 ± 0.60 | 2 | 11.02 ± 0.73 | 11.30 ± 0.80 |
| | | 15 | 10.33 ± 0.51 | 10.89 ± 0.73 |
| | | 37 | 9.36 ± 0.62 | 10.57 ± 0.56 |
| Cholesterol, mmol/l | 3.02 ± 0.08 | 2 | 2.77 ± 0.71 | 2.96 ± 0.52 |
| | | 15 | 2.01 ± 0.50 | 2.30 ± 0.57 |
| | | 37 | 2.48 ± 0.62 | 2.64 ± 0.46 |
| Creatinine, mkmol/l | 40.23 ± 2.84 | 2 | 47.38 ± 3.26 | 49.87 ± 8.12 |
| | | 15 | 45.59 ± 2.68 | 48.27 ± 12.29 |
| | | 37 | 46.84 ± 2.92 | 47.13 ± 9.82 |
| ALT, unit/l | 11.33 ± 1.96 | 2 | 10.84 ± 2.02 | 11.23 ± 1.70 |
| | | 15 | 7.63 ± 1.95 | 9.48 ± 1.85 |
| | | 37 | 8.98 ± 2.43 | 9.56 ± 1.34 |
| AST, unit/l | 19.13 ± 1.02 | 2 | 20.41 ± 3.06 | 20.13 ± 2.95 |
| | | 15 | 19.49 ± 2.90 | 15.14 ± 1.58 |
| | | 37 | 19.97 ± 2.78 | 18.21 ± 1.87 |
| Alkalinous phosphatase, unit/l | 40.74 ± 1.57 | 2 | 42.12 ± 4.23 | 43.4 ± 2.12 |
| | | 15 | 40.74 ± 6.78 | 41.60 ± 2.26 |
| | | 37 | 41.86 ± 5.26 | 42.18 ± 2.34 |
| Bilirubin, mmol/l | 35.93 ± 2.19 | 2 | 44.38 ± 4.12 | 42.56 ± 7.56 |
| | | 15 | 43.07 ± 3.57 | 40.69 ± 15.75 |
| | | 37 | 42.17 ± 3.28 | 41.45 ± 7.18 |

TABLE 14

Indexes of urine of the rats 1 month after the administration of the compounds according to the invention in the form of suppositories

| Index | Control | Compound | Dose 50 mg/kg | Dose 500 mg/kg |
|---|---|---|---|---|
| Protein, g/l | 0.74 ± 0.26 | 2 | 0.69 ± 0.33 | 0.76 ± 0.31 |
| | | 15 | 0.71 ± 0.274 | 0.87 ± 0.24 |
| | | 37 | 0.70 ± 0.19 | 0.72 ± 0.14 |
| Urea, mmol/l | 472 ± 140 | 2 | 457 ± 144 | 492 ± 187 |
| | | 15 | 413 ± 128 | 485 ± 131 |
| | | 37 | 427 ± 137 | 489 ± 152 |
| Glucose, Mmol/l | <6 | 2 | <5 | <5 |
| | | 15 | <6 | <6 |
| | | 37 | <5 | <5 |
| Potassium, g/l | 5.96 ± 1.1 | 2 | 5.78 ± 1.7 | 6.24 ± 1.8 |
| | | 15 | 5.28 ± 1.5 | 6.13 ± 1.6 |
| | | 37 | 6.12 ± 1.4 | 6.44 ± 1.3 |
| Sodium, g/l | 0.9 ± 0.1 | 2 | 1.7 ± 0.3 | 1.27 ± 0.3 |
| | | 15 | 1.2 ± 0.4 | 0.64 ± 0.4 |
| | | 37 | 1.4 ± 0.2 | 0.88 ± 0.4 |
| Urobilinogen, Mkmol/l | <17 | 2 | <16 | <16 |
| | | 15 | <17 | <17 |
| | | 37 | <15 | <15 |
| pH | 6.2 ± 0.3 | 2 | 6.1 ± 0.3 | 6.2 ± 0.2 |
| | | 15 | 6.3 ± 0.4 | 6.2 ± 0.3 |
| | | 37 | 6.4 ± 0.4 | 6.2 ± 0.3 |
| Bilirubin, Mkmol/l | <5 | 2 | <5 | <5 |
| | | 15 | <5 | <5 |
| | | 37 | <5 | <5 |
| Ketone bodies Mmol/l | <1 | 2 | <1 | <1 |
| | | 15 | <1 | <1 |
| | | 37 | <1 | <1 |

In the course of administration of preparations all groups of animals irrespective of the preparation dose were in stable clinical state without any signs of intoxication; the appearance and behavioral reactions were usual for healthy rats, the consumption of feed and water corresponded to the physiological norm.

From the results of investigations given in Tables 12, 13, 14, it is evident that 1 month after the administration of the suppository compounds according to the invention no changes in the indexes of the peripheral blood of the animals were found. 2 months after the administration of the suppositories no reliable difference in the indexes of peripheral blood of the animas received suppositories in a dose of 50 mg/kg was found. Concerning the animals received suppositories in a dose of 500 mg/kg, some changes were found, in particular the total amount of erythrocytes, hemoglobin, haematocrite value and an average volume of erythrocytes, in some cases a decrease of time of blood coagulation compared to the control value was observed.

The study of the biochemical indexes of blood serum and urine after long-time administration of the compounds according to the invention in suppositories has not revealed any difference between experimental and control animals.

The pathologoanatomic study one month after the beginning of administration suppositories and upon termination of the complete course of the treatment have shown that during the postmortem examination an identical picture without features of pathology was found out: the woolen integument was sleek, bright; the hypodermic fatty tissue was moderately evident. The lungs—airy of a light pink color, from the parenchyma section a small amount of a foamy reddish liquid flows down. The liver is elastic of a usual shape, the edges of the organ are slightly rounded, the capsule is sleek, bright, the tissue of the organ at the section is dark red, plethoric, bright. The kidneys are surrounded with a mild amount of fatty tissue, have beanlike shape, elastic, and the capsule is bright, clean and is easily taken out. The cortical and cerebral substance have a usual pattern with an expressed dividing boundary, the pelvis contains a small amount of a transparent, slightly opalescent liquid. The epinephroses are of a spherical shape, at the section are clearly differentiated in a lighter cortical substance and a dark cerebral substance. The spleen is elongated with a bright capsule, the pulp is of dark-cherry color, an insignificant amount of tissue and blood-like liquid being scrapable from the section surface. The thick intestine has a small amount of mucus with no signs of inflation, the vascular pattern is slightly expressed, the mucous tunic are clean without mucosal ulceration, the fecal mass in the end organ are formed. The testicles are of an oval shape of a dense consistence, with a slightly expressed vascular grid.

The dynamics of mass of the rat body during the administration of the preparations (1 to 9 weeks) was positive and did not differ from the dynamics in the control group.

The investigations were also aimed at the presence of irritating action of the suppositories on the mucosa of intestine and resorptive action: on rats with a mass of the organ of 169±7 g, the dose of 500 mg/kg being introduced once, the postmortem examination was made 30 minutes, 2 hours and 24 hours after the administration of the suppository. During the study of the rectum a small amount of mucus was found in the intestine lumen with the absence of an edema or hyperemia of the mucosa.

The irritating action of the suppositories on the eye mucosas was also studied on 5 rabbits of the chinchilla breed with a mass of 2.6 to 2.9 kg; the administration of a preparation in an amount of 75 mg at 37-38° C. into a lachrymal sac of one eye, and the effect was observed in 15, 30, 60 and 120 minutes after the administration and then for 24 hours. Any inflammatory phenomena were not found and there were no lachrymation, edemas or injections of the sclera vessels and conjunctiva.

In addition, the irritating action of the suppositories on the skin was determined: the preparation containing compounds according to the invention in suppository mass heated to 37-38° C. in an amount of 1000 mg was applied on skin sections sized 2×2 cm 10 of rats with a body mass of 175±6 g and 6 caves with a body mass of 235±17 g with a white wool. The duration of the application was 4 hours. Skin hyperlipemia, thickening of the skinfold or other features of irritation were not observed. During the application period and 24 hours after it no changes of the clinical state of the experimental animals was not found.

Thus, the absence of local irritation and toxic resorptive action of the preparations containing compounds according to the invention has not bee found during a single application in a considerable dose.

It should be clear for those skilled in the field of medicine and bioorganic chemistry that above-described properties of the compounds according to the invention can manifest themselves also in normalization of other processes arising in an organisms and associated with metabolic acidosis and an effect of an excessive quantity of free-radical forms of oxygen, in particular, uncontrollable inflammations, uncontrollable proteolysis, poor activity of the enzyme of helicase responding for untwisting the DNA duplex in a replicative zone of uncontrollable oxidation-reduction processes, processes of a premature aging of an organism effecting on the electronic-proton processes in the mitochondrion and on functioning of the respiratory system.

The application of the cyclic bioisosteres of derivatives of a purine system according to the invention or their pharmacologically acceptable salts as active ingredients of a pharmaceutical composition allows one to produce pharmaceutical compositions in a wide range of practical application.

In so doing they render normalizing effect on the vital systems of an organism, which can be predicted and chosen optimal depending on the indications, an amount of active ingredient in a medicinal preparation, a dose, and conditions of a drug intake.

Pharmaceutically acceptable salts of cyclic bioisosteres of derivatives of a purine system, according to the invention may be salts of pharmaceutically acceptable metals such as lithium, sodium, potassium, calcium, barium, silver, as well as salt pharmaceutically acceptable acids such as hydrochlorides, sulfases, acetases, hydrobromides, phosphases, succinates, maleates, fumarates, citrases, gluconates, methylsulphonates, n-toluenesulphonates. The pharmaceutically acceptable salts can be obtained by reacting cyclic bioisosteres of derivatives of a purine system with corresponding acids or bases.

The active ingredient of the pharmaceutical composition according to the invention may comprise a composition of several compounds according to the invention, for example, salts of alkaline and/or alkaline-earth metals, for example, a composition of sodium and potassium salts, sodium and lithium and others, which are well compatible among themselves and, depending on their biological activity, can increase the duration of action of the medicinal preparation in an organism.

The pharmaceutical composition based on the compounds according to the invention can be a solution of an active ingredient in pharmaceutically acceptable liquid carrier, for example, water, a physiological solution, buffer solutions or compatible with ingredients enhancing their solubility.

The pharmaceutical composition can represent can be a fine powder of an active ingredient suitable for application in solutions for injections, in applications or used for preparation of various medicinal forms.

The oral administration is usually a preferable way for administration of medicinal agents into an organism, as this way is the most convenient and acceptable for the patient. The compositions according to the invention can be made as agents for oral administration, for example, tablets, granules, globules, powders, capsules, ampoules, suspensions, emulsions. In so doing the pharmaceutical composition may in addition contain agents for rising bioavailability, for example, microcrystalline cellulose that allows one to reduce the contents of biologically active ingredient in a single drug dose, or, besides, may be made as a spontaneously dispersed concentrate which, when mixed with distilled water or physiological solution of cooking salt, creates aqueous microemulsions with a stable phase and increased ability of infiltration and diffusion.

It is desirable in the treatment of acute states that the pharmaceutical composition has fast and consecutive action and good biological compatibility of the components of the composition and the medium.

The fast absorption of the active ingredient can be achieved by a parenteral injection that is traditional for clinical conditions but it is unacceptable for self-treatment. In this case, an effective way of administration of a medicinal agent in an organism through rectum using clusters, soft gelatinous capsules or suppositories, for example, as solid dosed forms with a suitable configuration which either melt at a human body temperature or are dissolved or disperse in the mucous secretion cavity. The cyclic bioisosteres of a derivative purine system according to the invention are well combined with known components and ingredients used for manufacture of medicinal preparations.

The medical experts know that for improvement of the adsorption of biologically active substances having poor solubility in water or in any selective media, the active ingredient of a pharmaceutical composition in the form of a saturated solution, in a solid form can be encapsulated in one or more plate membrane containing lipids, for example, in liposomes, allowing the active ingredient to be delivered to a specific region.

According to the invention, in the pharmaceutical composition derivatives of phthalhydrozines and their salts can be contained in a liposomal form, for example, in a multiphase liposom system of delivery of medicines, which is stable and can be easily diluted in water, varying the state of the pharmaceutical composition from a state of a diluted liquid up to a gelatinous state that is important for derivative compounds, which in the initial condition are poorly soluble in the gastrointestinal path medium, as well as expands a possibility of application of higher doses of the active ingredient to be introduced orally.

Besides in the pharmaceutical composition according to the invention the pharmaceutically the acceptable carrier may represent a composition containing pharmaceutically active additives.

In so doing, according to the invention, in the pharmacologically active additives may be selected from the group including stabilizing agents, dispensers, aromatizers, emulsifiers, conductors, bioavailability rising agents, one of which can be an agent for increasing solubility of not readily soluble compounds, for example, solvent of dimethylsulfoxide (DMSO).

In many diseases it is expedient to use different methods of local action on a pathological process, especially in presence of contraindication to general therapy, for example, at appreciable disorder of the vital organs. One of the methods of local treatment is application of external medicinal agents.

It is known that, proceeding from the skin sensitivity, probability of its irritation and transdermal absorptivity (skin hygroscopic capacity), pH of the pharmaceutical preparation for external application should be kept in a range of 4-8, preferably, in a range of 5-7. When pH is too low (pH 3 and lower), its high acidity initiates a strong skin irritation. When pH is too high (pH 9 and higher), the transdermal absorptivity of the active ingredient is reduced, the skin irritation rises up.

In order to increase the transdermal absorptivity (suction) of the active ingredient, the pharmaceutical preparation can be mixed with the so-called amplifiers of absorption, for example, organic bases such as triethanolamin, crotamiton, esters of fatty acids with an average chain length, 1-menthol, benzalcohol and similar substances. The organic base facilitates the release of the active ingredient from the base, because it makes the compound more water-soluble due to the formation of salts. The organic base acts as a regulator of pH of a medicinal preparation.

pH of a medicinal agent can also be adjusted by alkaline compounds (potassium hydroxide and sodium hydroxide, triethanolamine, diisopropanolamine, monoethanolamit, etc.

The solutions of the metal salts of the compounds according to the invention have pH=7-8, the solutions of hydrochlorides, acetates, phosphases, hydrobromides, nitrates, sulfases and other organic salts of the compounds according to the invention have pH=4-7 that provides good prospects of creation of medicinal agents for external application.

In so doing a pharmaceutical composition for external application may represent a gel-emulsion containing as an active ingredient a bioisostere derivative of a purine system according to the invention, hydrophylic polymer, oily substance, a nonionic surface-active agent, an alkaline compound or an organic base as a pH regulator of the medium and water. In this case, the bioisosteres of derivatives of a purine system according to the invention are chemically compatible with these ingredients.

The pharmaceutical composition according to the invention can be made, for example, in the form of a disappearing emulsion including higher alcohol, hydrocarbon, ester of fatty acid, polyol or alkali, an antiseptic agent, water and other ingredients.

The pharmaceutical compositions can be based on of the compounds according to the invention, for example, in the form of gels formed by means of gel-forming derivatives of cellulose, for example, oxyethylcellulose, oxypropylcellulose, carboxymethylcellulose and other derivative containing starch, gelatine, synthetic polymers, for example, polyvinylpyrolidone, polyethyleneglycol, moistening agents such as polyatomic alcohols, for example, glycerin, 1,3-butyleneglycol, propyleneglycol, dipropyleneglycol, etc.

The pharmaceutical composition based on bioisosteres of derivatives of a purine system according to the invention can be hydrophylic ointment or water-absorbing ointment emulsion containing petrolatum oil, liquid paraffin, surface-active compounds, for example, esters of sorbitane and fatty acids (sorbitanemonostearate and ethers), esters of glycerin and fatty acids (glycerylmonostearate, diglycerylmonooleate, etc), esters of polyoxyethylenesorbitane and fatty acids (polyoxyethylenemonostearate and others), esters of polyethylene glycol and fatty acids, polyethylene hydrogenized castoric oil, mixture of these substances, and other components, for example, higher alcohol such as hydrocarbon, for example, paraffin, ceresine, cetyl alcohol (cetanol), stearyl alcohol, oleyl alcohol, behenolic alcohol, ethers of a fatty acid, for example, stearin, oleic, polyatomic alcohol, oil and vegetable fats, for example, olive, castoric oil, animal fats (beef and pork lard, horse fat and other fats), mineral wax, beeswax, as well as antiseptic, for example, methylparaben, propylparaben and water.

Industrial Applicability

The application of cyclic bioisosteres of derivatives of a purine system according to the invention or their pharmacologically acceptable salts as active ingredients of a pharmaceutical composition allows one to produce pharmaceutical compositions of a wide range of application with the use of the therapeutic effect caused by the inherent properties of the cyclic bioisosteres of a purine system according to the invention.

The invention claimed is:

1. A method for treating acidosis in a subject, said method comprising administering to the subject in need of such treatment a pharmaceutically-effective amount of a biologically-active compound, wherein said biologically-active compound has a general structural formula:

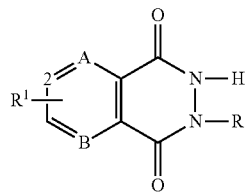

where R is selected from the group consisting of

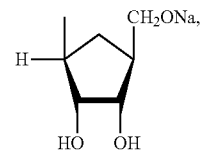

Li, Na, and K;

$R^1$ is selected from the group consisting of —H, —$NH_2$, —Br, —Cl, —OH, and —COOH;

B is selected from the group consisting of —CH=, and —$CR^1$=;

Z is selected from the group consisting of —CH=, and —$CR^1$=; and

A is selected from the group consisting of —CH=, and —$CR^1$=, wherein when A is —$CR^1$=, then B is —CH= and Z is —CH=, and pharmacologically acceptable salts thereof, wherein the acidosis is not caused by hypoxia.

2. The method as claimed in claim 1, wherein said method decreases aggregation of thrombocytes.

3. The method as claimed in any of claim 1 or 2, wherein the cyclic bioisostere is a derivative of benzo[d]-3H-pyridazine-1,4-dione, having a general formula

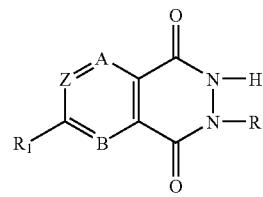

where R selected from the group consisting of the atom of Li, Na, K, and

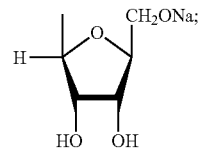

and $R^1$ is selected from the group consisting of —H, —$NH_2$, —Cl, OH, and —COOH.

4. The method as claimed in claim 3, wherein the biologically-active compound is selected from the group consisting of:

sodium salt of 2-(β-D-ribofuranosile)benzo[d]-3H-pyridazine-1,4-dione, sodium salt of 5-amino-2-(β-D-ribofuranosile)benzo[d]-3H-pyridazine-1,4-dione, sodium salt of 6-amino-2-(β-D-ribofuranosile)benzo[d]-3H-pyridazine-1,4-dione, sodium salt of 5-chlorine-2-(β-D-ribofuranosile)benzo[d]-3H-pyridazine-1,4-dione, disodium salt of 5-hydroxy-2-β-D-ribofuranosile)benzo[d]-3H-pyridazine-1,4-dione, lithium salt of 5-amino-benzo[d]-3H-pyridazine-1,4-dione, sodium salt of 5-amino-benzo[d]-3H-pyridazine-1,4-dione,
potassium salt of 6-amino-benzo[d]-3H-pyridazine-1,4-dione,
disodium salt of 5-hydroxy-benzo[d]-3H-pyridazine-1,4-dione, and
disodium salt of 6-carboxy-benzo[d]-3H-pyridazine-1,4-dione.

\* \* \* \* \*